United States Patent
Chambers et al.

(10) Patent No.: US 9,753,007 B1
(45) Date of Patent: *Sep. 5, 2017

(54) ISOTACHOPHORETIC FOCUSING OF NUCLEIC ACIDS

(71) Applicant: The Board of Trustees of the Leland Stanford Junior University, Palo Alto, CA (US)

(72) Inventors: Robert D. Chambers, Lebanon, NH (US); Juan G. Santiago, Stanford, CA (US); Alexandre Persat, Princeton, NJ (US); Reto B. Schoch, Gais (CH); Mostafa Ronaghi, Menlo Park, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/497,050

(22) Filed: Sep. 25, 2014

Related U.S. Application Data

(63) Continuation of application No. 12/716,142, filed on Mar. 2, 2010, now Pat. No. 8,846,314.
(Continued)

(51) Int. Cl.
*C12Q 1/68* (2006.01)
*G01N 27/447* (2006.01)

(52) U.S. Cl.
CPC .................. *G01N 27/447* (2013.01)

(58) Field of Classification Search
None
See application file for complete search history.

(56) References Cited

U.S. PATENT DOCUMENTS

| 3,869,365 A | 3/1975 | Sunden |
| 3,948,753 A | 4/1976 | Arlinger |

(Continued)

FOREIGN PATENT DOCUMENTS

| EP | 1742057 A1 | 1/2007 |
| WO | 2008053047 A2 | 5/2008 |

(Continued)

OTHER PUBLICATIONS

US 7,247,224, 07/2007, Weber (withdrawn)
(Continued)

*Primary Examiner* — Betty Forman
(74) *Attorney, Agent, or Firm* — Brian E. Davy; Bozicevic, Field & Francis LLP

(57) ABSTRACT

A method and system are presented for fast and efficient isolation, purification and quantitation of nucleic acids from complex biological samples using isotachophoresis in microchannels. In an embodiment, a sieving medium may be used to enhance selectivity. In another embodiment, PCR-friendly chemistries are used to purify nucleic acids from complex biological samples and yield nucleic acids ready for further analysis including for PCR. In another embodiment, small RNAs from biological samples are extracted, isolated, preconcentrated and quantitated using on-chip ITP with a high efficiency sieving medium. The invention enables fast concentration and separation (takes 10s to 100s of seconds) of nucleic acids with high selectivity and using lower volumes of reagents (order of 10s of µL to focus less than 1 µg/µL of nucleic acid).

41 Claims, 13 Drawing Sheets

Related U.S. Application Data

(60) Provisional application No. 61/209,199, filed on Mar. 3, 2009.

(56) References Cited

U.S. PATENT DOCUMENTS

| | | | |
|---|---|---|---|
| 4,897,169 | A | 1/1990 | Bier et al. |
| 4,900,677 | A | 2/1990 | Hewitt |
| 5,447,612 | A | 9/1995 | Bier et al. |
| 5,464,515 | A | 11/1995 | Bellon |
| 5,817,225 | A | 10/1998 | Hinton |
| 5,939,291 | A | 8/1999 | Loewy et al. |
| 6,685,813 | B2 | 2/2004 | Williams et al. |
| 6,695,009 | B2 | 2/2004 | Chien et al. |
| 6,780,584 | B1 | 8/2004 | Edman et al. |
| 6,818,113 | B2 | 11/2004 | Williams et al. |
| 6,934,836 | B2 | 8/2005 | Strand et al. |
| 6,935,772 | B2 | 8/2005 | Karp et al. |
| 7,214,299 | B2 | 5/2007 | Armstrong |
| 7,223,325 | B2 | 5/2007 | Landers et al. |
| 7,316,771 | B2 | 1/2008 | Weber |
| 7,371,533 | B2 | 5/2008 | Slater et al. |
| 7,399,394 | B2 | 7/2008 | Weber |
| 7,473,551 | B2 | 1/2009 | Warthoe |
| 7,494,577 | B2 | 2/2009 | Williams et al. |
| 7,517,442 | B1 | 4/2009 | Champagne |
| 7,635,563 | B2 | 12/2009 | Horvitz et al. |
| 7,951,278 | B2 | 5/2011 | Santiago et al. |
| 8,017,408 | B2 | 9/2011 | Meinhart et al. |
| 8,021,531 | B2 | 9/2011 | Park et al. |
| 8,133,371 | B2 | 3/2012 | Marziali et al. |
| 8,277,628 | B2 | 10/2012 | Ronaghi et al. |
| 8,394,251 | B2 | 3/2013 | Santiago et al. |
| 8,846,314 | B2 * | 9/2014 | Chambers ............ C12N 15/101 204/450 |
| 2002/0079223 | A1 | 6/2002 | Williams et al. |
| 2002/0189946 | A1 | 12/2002 | Wainright et al. |
| 2004/0031683 | A1 | 2/2004 | Eipel et al. |
| 2005/0079519 | A1 * | 4/2005 | Boles ................... C12Q 1/6816 435/6.12 |
| 2005/0121324 | A1 | 6/2005 | Park et al. |
| 2005/0133370 | A1 | 6/2005 | Park et al. |
| 2005/0170362 | A1 | 8/2005 | Wada et al. |
| 2006/0019286 | A1 | 1/2006 | Horvitz et al. |
| 2006/0042948 | A1 | 3/2006 | Santiago et al. |
| 2006/0078998 | A1 | 4/2006 | Puskas et al. |
| 2006/0254915 | A1 | 11/2006 | Hirokawa et al. |
| 2007/0026439 | A1 | 2/2007 | Faulstich et al. |
| 2008/0020386 | A1 | 1/2008 | Chen et al. |
| 2008/0021674 | A1 | 1/2008 | Puskas |
| 2008/0156080 | A1 | 7/2008 | Balgley |
| 2008/0166770 | A1 | 7/2008 | Morita et al. |
| 2009/0178929 | A1 | 7/2009 | Broer et al. |
| 2010/0116657 | A1 | 5/2010 | Fiering et al. |
| 2010/0209927 | A1 | 8/2010 | Menon et al. |
| 2010/0224494 | A1 | 9/2010 | Chambers et al. |
| 2010/0261612 | A1 | 10/2010 | Young |
| 2010/0270157 | A1 | 10/2010 | Kurosawa et al. |
| 2010/0294663 | A1 | 11/2010 | Weber |
| 2010/0323913 | A1 | 12/2010 | Young et al. |
| 2011/0024296 | A1 | 2/2011 | Park et al. |
| 2011/0036718 | A1 | 2/2011 | Jung et al. |
| 2011/0174624 | A1 | 7/2011 | Weber |
| 2011/0220499 | A1 | 9/2011 | Chambers et al. |
| 2011/0297546 | A1 | 12/2011 | Schoch |
| 2012/0061242 | A1 | 3/2012 | Santiago et al. |
| 2012/0152746 | A1 | 6/2012 | Santiago et al. |
| 2012/0160689 | A1 | 6/2012 | Utz et al. |
| 2012/0175258 | A1 | 7/2012 | Mariella, Jr. |

FOREIGN PATENT DOCUMENTS

| | | |
|---|---|---|
| WO | 2009079028 A1 | 6/2009 |
| WO | 2010026222 A1 | 7/2011 |

OTHER PUBLICATIONS

Chen, et al., Determination of Binding Constants by Affinity Capillary Electrophoresis, Electrospray Ionization Mass Spectrometry and Phase-distribution Methods, Trends Analyt Chem., Oct. 2008, 27(9); 738-748.

Gohring, et al. The scaffold/matrix attachment region binding protein hnRNP-U (SAF-A) is directly bound to chromosomal DNA in vivo: a chemical cross-linking study. Biochemistry. Jul. 8, 1997;36(27):8276-83.

Hinckley, J. O. N., Transphoresis and Isotachophoresis—Automatable Fast Analysis of Electrolytes, Proteins, and Cells, with Supression of Gravitational Effects, Clinical Chemistry, vol. 20, No. 8, 1974, 973-991.

Jung, et al., On-chip Millionfold Sample Stacking Using Transient Isotechophoresis, Analytical Chemistry, vol. 78, No. 7, Apr. 1, 2006, 2319-2327.

Khurana, et al., Effects of Carbon Dioxide on Peak Mode Isotachophoresis: Simultaneous Preconcentration and Separation, Lab Chip, 2009, 9, 1377-1384.

Khurana, et al., Preconcentration, Separation, and Indirect Detection of Nonfluorescent Analytes Using Fluorescent Mobility Markers, Analytical Chemistry, vol. 80, No. 1, Jan. 1, 2008, 279-286.

Khurana, et al., Sample Zone Dynamics in Peak Mode Isotachophoresis, Analytical Chemistry, Published on Web, Jul. 22, 2008, pp. A-H.

Kitagawa, et al., High-speed Analysis of Proteins by Microchip Isoelectric Focusing with Linear-imaging UV Detection, Analytical Sciences, Aug. 2009, vol. 25, 979-984.

Kondratova, et al., Concentration and Isolation of DNA from Biological Fluids by Agarose Gel Isotachophoresis, Biotechniques, vol. 39, No. 5, Nov. 2005, 695-699.

Liu, et al. "Isotachophoresis preconcentration integrated microfluidic chip for highly sensitive genotyping of the hepatitis B virus" J of Chromatography B, 2006, 844: 32-38.

Morio, et al. Quantitative analysis of trifluoroacetate in the urine and blood by isotachophoresis. Anesthesiology. Jul. 1980;53(1):56-9.

MOWIO—History/Manufacture/Structure, p. A1-no date available.

Persat, et al., Purification of Nucleic Acids from Whole Blood Using Isotachophoresis, Analytical Chemistry, vol. 81, No. 22, Nov. 15, 2009, 9507-9511.

Prest et al "Miniaturised isotachophoresis of DNA" J. of Chromatography A, 2007, 1156: 154-159.

Schoch, et al., Rapid and Selective Extraction, Isolation, Preconcentration, and Quantitation of Small RNAs from Cell Lysate Using On-chip Isotachophoresis, Lab Chip, 2009, 9, 2145-2152.

* cited by examiner

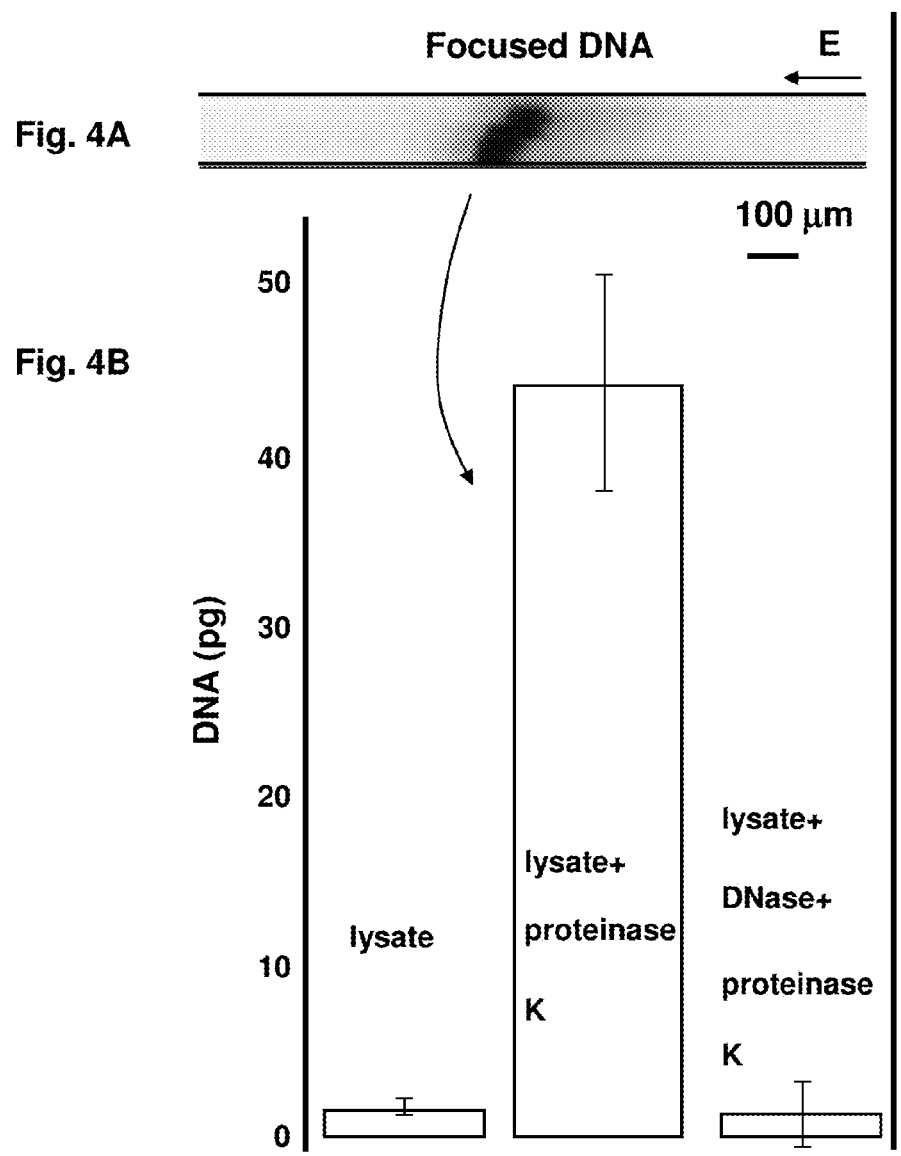

Fig. 7A  Filling of microchannel with matrix
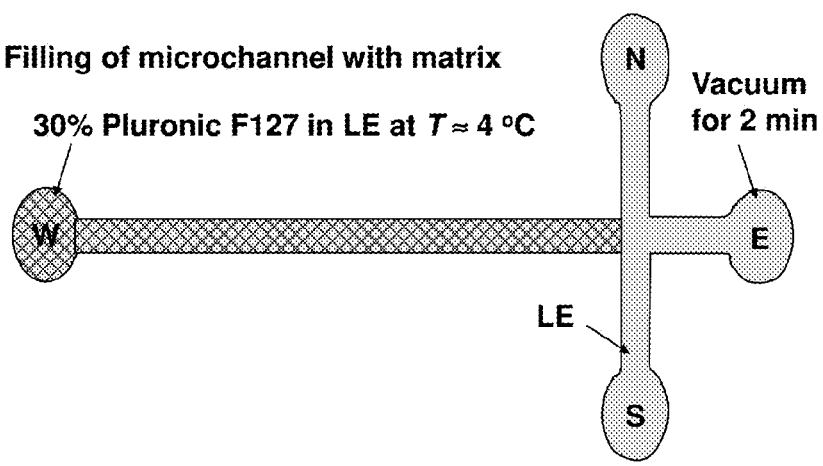
Fig. 7B  After 10 min at $T \approx 4$ °C
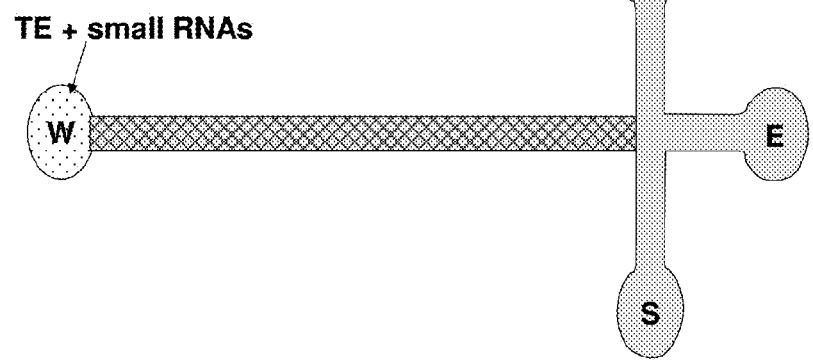
Fig. 7C  ITP focusing of small RNAs
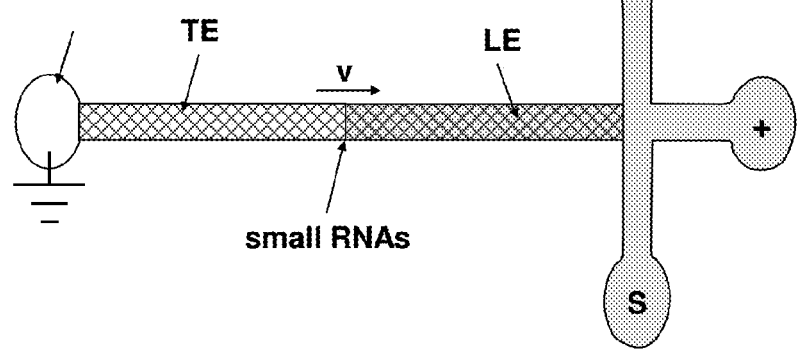

US 9,753,007 B1

ISOTACHOPHORETIC FOCUSING OF NUCLEIC ACIDS

CROSS-REFERENCE TO RELATED APPLICATIONS

This application is a continuation application of U.S. patent application Ser. No. 12/716,142, filed Mar. 2, 2010, which claims priority from U.S. Provisional Patent Application No. 61/209,199, filed Mar. 3, 2009, both of which are hereby incorporated by reference in their entireties.

STATEMENT OF GOVERNMENTAL SUPPORT

This invention was made with Government support under Contract N01-HV-28183 awarded by the National Institutes of Health. The Government has certain rights in this invention.

REFERENCE TO SEQUENCE LISTING, COMPUTER PROGRAM, OR COMPACT DISK

This application contains a Sequence Listing which has been submitted as an ASCII text file and is hereby incorporated by reference in its entirety. This text file was created on Sep. 11, 2014, is named 3815_80_2_Sequence.txt, and is 815 bytes in size.

BACKGROUND OF THE INVENTION

Field of the Invention

The present invention relates to the field of isotachophoresis (ITP), particularly for selective separation, detection, extraction, pre-concentration or quantitation of RNA, DNA, and/or other biological molecules.

Related Art

Presented below is background information on certain aspects of the present invention as they may relate to technical features referred to in the detailed description, but not necessarily described in detail. That is, individual parts or methods used in the present invention may be described in greater detail in the materials discussed below, which materials may provide further guidance to those skilled in the art for making or using certain aspects of the present invention as claimed. The discussion below should not be construed as an admission as to the relevance of the information to any claims herein or the prior art effect of the material described.

Microfluidics has become an alternative to traditional techniques for biological and medical analysis and offers the use of small reagent volumes, fast analyses, and the potential for parallelization. 1 Polymerase chain reaction (PCR), capillary electrophoresis, 3 immunoassays, 4 and many other analytical techniques used in biology and medicine have been successfully miniaturized. However, sample preparation is often still a challenge and a limiting factor in the capability of many devices, so that most miniaturized systems have used prepurified, ideal samples as analyte. One important application is the purification of nucleic acids (NA) from complex biological samples, i.e., a complex mixture of macromolecules, which may contain small molecules as well. We here demonstrate a simple, fast, efficient, and sensitive technique for the purification of NA from whole blood which leverages the physicochemistry of isotachophoresis (ITP). The standard method for NA purification is based on solid phase extraction (SPE). For example, commonly used QIAGEN (Valencia, Calif.) purification columns rely on the adsorption of NA on silica membranes. 6 Extensive work by Landers and co-workers has shown successful microchip integration of SPE with application to purification of DNA7 and RNA8 and successful integration with on-chip PCR. While micro-SPE shows excellent efficiency and throughput, the process requires specialized materials and fabrication (e.g., micropillars or packing of silica beads). Further, the typical SPE protocol involves three successive steps (loading, washing, elution), requires bulk flow control, and uses a PCR inhibiting chemistry (e.g., chaotropic agents, organic solvents). Another example of SPE is the Quick Gene Mini-80, a nucleic acid extraction device by Fujifilm Life Sciences which uses pressurized filtration accompanied by washing and eluting steps to isolate nucleic acids.

ITP is a well-established separation and preconcentration technique. It leverages a heterogeneous buffer system to generate strong electric field gradients, allowing simultaneous focusing and separation of ionic species based on their effective electrophoretic mobilities. ITP has been marginally used as a sample purification method. For instance, Caslayska et al. (Caslayska, J.; Thormann, W. J., *Chromatogr.*, A 1992, 594, 361-369) used ITP to simultaneously purify and isolate proteins. Kondratova et al (Kondratova, V. N.; Serd'uk, O. I.; Shelepov, V. P.; Lichtenstein, A., *Biotechniques*, 2005, 39, 695-699) concentrated and isolated extracellular DNA from blood plasma and urine by agarose gel ITP with applications to cancer diagnosis. This ITP isolation procedure yields DNA in an agarose gel slab which requires further purification steps prior to analysis. To our knowledge, ITP has never been applied to sample preparation from biological samples for analysis. The method in our invention is capable of accepting into the on-chip process a complex biological sample like whole blood added directly to the ITP well without pre-processing like centrifugation or filtration.

Presented below is an ITP-based purification method for extracting genomic DNA from a biological sample such as whole blood lysate as a sample. Previous work has been directed towards methods in which a complex sample such as this, containing a mixture of macromolecules, is pre-treated prior to ITP. In addition to separating Genomic DNA from cellular components such as membranes, organelles, proteins, and other nucleic acids.

In addition, the present methods relate to separation of small RNAs from other nucleic acids (sometimes referred to as polynucleic acids, as opposed to single nucleotides).

Small RNAs are involved in RNA interference (RNAi). RNAi refers to the regulation of gene expression, in which small RNAs mediate gene silencing. In the RNAi process small RNAs are loaded onto Argonaute proteins at the core of an RNA-induced silencing complex (RISC), where these noncoding RNAs guide the sequence-specific silencing of transcripts through base-pairing interactions. The transcripts are typically messenger RNAs (mRNAs), which are cleaved or prevented from being translated by ribosomes, leading to their degradation. In humans at least 30% of the genes are thought to be regulated by miRNAs, which tune protein synthesis from thousands of genes. Further, miRNAs have recently been linked with common diseases.

miRNA expression profiling has been done using Northern blotting but this technique involves laborious, time-consuming procedures and lacks automation. The method of reverse transcription polymerase chain reaction (RT-PCR) is typically restricted to the quantitation of specifically lengthened miRNAs or pre-miRNAs, because the short length of miRNAs significantly limits the flexibility of primer design. Microarrays allow profiling miRNAs in a highly efficient parallel fashion, but this technique has encountered difficulties in reliably amplifying miRNAs without bias.

To overcome the obstacle of selective and sensitive quantitation devices for miRNA research, various techniques have been developed: a nanogapped microelectrode-based biosensor array; electrocatalytic nanoparticle tags and gold nanoparticle probes; and capillary electrophoresis with the sieving matrices of poly(ethylene oxide) or poly(vinyl pyrrolidone) for miRNAs, and poly(ethylene glycol) for general oligonucleotides applications. Compared to conventional capillary electrophoresis, microchip electrophoresis techniques offer considerably shorter analysis times, the ability to work with small sample volumes, and the opportunity of combination with additional on-chip assay steps. However, the loading of microchannels with gels remains challenging due to the high viscosity of crosslinked gels and consequential bubble formation.

Thus there exists a need in the field for fast and efficient method for extraction, isolation, preconcentration and quantitation of nucleic acids including small RNAs from complex biological samples like blood, blood lysate, cell culture, cell lysates, etc. For the present invention, we have extracted and purified nucleic acids from complex biological samples using ITP in microchannels and with PCR-friendly chemistries. We have extracted, isolated, preconcentrated and quantitated small RNAs from complex biological samples using ITP in microchannels loaded with a high efficiency sieving medium.

SPECIFIC PATENTS AND PUBLICATIONS

Jung et al., "On-Chip Millionfold Sample Stacking Using Transient Isotachophoresis," *Anal. Chem.*, 78:2319-2327 (2006) discloses on-chip ITP integrated with on chip capillary electrophoresis.

Persat et al., "Purification of Nucleic Acids from Whole Blood Using Isotachophoresis," *Anal. Chem.*, 81:9507-9511 (2009), published on the web Oct. 15, 2009, discloses certain work described here.

Khurana and Santiago, "Preconcentration, Separation, and Indirect Detection of Nonfluorescent Analytes Using Fluorescent Mobility Markers," *Anal. Chem.*, 80:279-286 (Nov. 22, 2007) discloses a technique which uses ITP for both preconcentration and separation. The authors employ a leading electrolyte (LE), trailing electrolyte (TE), and a set of fluorescent markers of mobilities designed to bound those of nonfluorescent analytes of interest.

US 2002/0079223 by Williams et al., entitled "Tandem Isotachophoresis/zone Electrophoresis Method and System," discloses a microfluidic device which may be used in ITP.

WO 2008/053047 by Weber et al., entitled "Novel methods, kits and devices for isotachophoresis applications," published 8 May 2008, discloses a method and device where the use of at least one T medium, at least one diluted T medium and at least one L medium according to the present invention provides an essentially constant pH over the whole width of the separation zone between the electrodes of an apparatus suitable to carry out an ITP separation.

Prest et al., "Miniaturised isotachophoresis of DNA," *J. Chromatog.*, 1156:154-159 (2007) discloses an electrolyte system comprising a leading electrolyte of 5 mM perchloric acid at pH 6.0 and a terminating electrolyte of 10 mM gallic acid used to perform isotachophoresis of DNA containing samples on a miniaturised poly(methyl methacrylate) device. Under such conditions it was found that no separation of DNA fragments was observed with the substance migrating instead as a single isotachophoretic zone.

Kondratova et al., "Concentration and isolation of DNA from biological fluids by agarose gel isotachophoresis," *BioTechniques*, 39:695-699 (November 2005) discloses that As a rule, isotachophoresis is not used for the separation of nucleic acids because the mobility of polynucleotides in this system does not depend on their size. There is also disclosed proposed method of agarose gel isotachophoresis of DNA has been used for the isolation of blood DNA.

Young et al. WO 2009/079028 published 25 Jun. 2009, entitled "Purification and concentration of proteins and DNA from a complex sample using isotachophoresis and a device to perform the purification," discloses a method of simultaneously co-purifying and concentrating nucleic acid and protein targets into a single volume. The sample is added to the middle of a device that allows isotachophoresis to occur in two directions toward both the positive and negative electrodes when a voltage is applied.

BRIEF SUMMARY OF THE INVENTION

The following brief summary is not intended to include all features and aspects of the present invention, nor does it imply that the invention must include all features and aspects discussed in this summary.

The present invention comprises, in certain aspects, methods and materials useful for fast and efficient extraction, isolation, preconcentration and quantitation of genetic material (e.g., nucleic acids) based on isotachophoresis techniques (ITP).

The invention may be characterized, in certain aspects, as an isotachophoretic method for concentrating a target nucleic acid from a sample containing a complex mixture of macromolecules, such as a complex biological mixture (e.g., blood). The target nucleic acid will typically be isolated from other macromolecules, or even small molecules, in a concentrated zone between the LE and the TE. It may be extracted from that zone in a purified form and used for further processing, such as PCR. The method comprises steps including treating the sample, if the target is contained in cells, with a cell lysis agent. The cell lysis agent may be mechanical, thermal, electrical or chemical, such as known cell lysis buffers, suitable for the type of cell being lysed. RBC lysis reagents are commercially available.

The method further involves, if the target nucleic acid is bound to protein, treating the sample with a release agent to release the target nucleic acid from the protein. The release agent may be a proteinase, such as proteinase K (EC 3.4.21.64). It can also be used for inactivation of RNAse and DNAse.

The method further comprises applying the treated sample to a sample well connected to a liquid channel. The sample well and liquid channel may be separate or integrally formed in a microfluidic chip. The channel may be an etched channel in a microfluidic device or a capillary tube. In further aspects, the present inventive method comprises contacting the treated sample from the sample well with a trailing electrolyte ("TE") having mobility greater than said macromolecules that are not target nucleic acid and a mobility less than said target nucleic acid; moving the treated sample from the sample well to the liquid channel, containing a leading electrolyte ("LE") that has a mobility greater than said target nucleic acid, wherein said LE and TE contain electrolytes in free solution, and are at pH between about 4 and 10. The pH may be between 6 and 9, or may change during the process and/or may be different between the LE and the TE. The method further comprises applying a voltage across the liquid channel containing said treated sample, LE and TE to cause concentration of said target nucleic acid in an isotachophoresis interface between LE and TE. The contacting of the treated sample with the TE may involve applying the sample and TE sequentially and/or mixing.

In certain aspects, the present inventive method also comprises methods where said applying to a sample well is to a sample well and liquid channel comprised in a microfluidic device. The separation and concentration may be achieved in micro-volumes over distances on the order of millimeters. In certain aspects, the present inventive method also comprises the step of adding a polymer sieving agent, such as a polymer, e.g., a block copolymer, a linear polymer of a branched polymer in the liquid channel to change mobility of one or both of target nucleic acids and molecules not to be isolated. Block copolymers contain repeating oligomers of two or more different polymers.

The invention may further comprise adding an agent for suppressing electroosmotic flow to the liquid channel. This agent may be selected from the group consisting of polylactams, substituted polyacrylamide derivatives, water-soluble methylhydroxyethyl derivatives of cellulose, polyvinylalcohol, polyvinylpyrrolidones and polyethyleneglycols. The polylactam may be polyvinylpyrrolidone.

In certain aspects, the present inventive method also comprises use of a device where the liquid channel divides at channel bifurcations to distribute various contents of said complex mixture to various channels. An example of this is illustrated in FIG. 13. Mixing may also be carried out where the sample is mixed with the TE. Mixing may be done off-chip, or on-chip by microfluidic means, e.g., as described in U.S. Pat. No. 6,935,772, issued Aug. 30, 2005.

In certain aspects, the present inventive method also comprises an isotachophoretic method for concentrating small RNA from a sample containing a mixture of macromolecules and longer RNA. Small RNA may be regarded as RNA smaller than mRNA or tRNA. Major types of small RNA molecules are small nuclear RNA, small nuclear RNA, micro RNA (miRNA) and short interfering RNA (siRNA). Both miRNA and siRNA are about 20-25 nucleotides long. In this method, if the sample contains cells, one treats the sample with a cell lysis agent, to obtain a treated sample. The method further comprises applying the treated sample from the previous step to a sample well connected to a liquid channel; contacting the treated sample from the sample well with a trailing electrolyte ("TE") having mobility less than said small RNA; moving the treated sample from the sample well to a liquid channel with a leading electrolyte ("LE") that has a mobility greater than said small RNA, wherein (e) said LE and TE contain electrolytes in free solution, and are at a pH which causes effective mobility of proteins to be different from that of the small RNA; adding a sieving agent to the LE; and applying a voltage across the liquid channel containing said treated sample, LE and TE to cause concentration of the small RNA in an isotachophoresis interface between LE and TE.

The method may further comprise the step of treating the sample with an RNAse inhibitor. RNAse may be inhibited by an enzyme that degrades proteins, or by placental protein, antibodies, or commercial products such as RNAse inhibitor from Thermo Scientific. The method may also employ a sieving agent, which may be a polymer, including a block copolymer of ethylene oxide and propylene oxide. The method may further comprise the step of treating the sample with one or more enzymes selected from the group consisting of DNAse and proteinase, which may be proteinase K. In addition, a protein denaturing agent may be added to the liquid channel.

BRIEF DESCRIPTION OF THE DRAWINGS

FIGS. 4A and 4B are an illustration of focused DNA in a microchannel; FIG. 4B is a graph showing results of ITP based nucleic acid purification from human blood, in FIG. 4A focused pg of DNA for different sections of a separation channel are shown.

FIGS. 7A, 7B and 7C are schematic of microchip and protocol for loading Pluronic F-127 and extracting, isolating, concentrating and quantitating small RNAs using ITP. 7A shows filling of the microchannel with sieving agent and LE, at 4° C.; 7B shows addition of small RNAs and TE at +10 min, with temp. 22° C.; and 7C shows ITP focusing of small RNA in the channel between the West and East wells and between the LE and the TWE; RNAs have migrated towards the anode.

DETAILED DESCRIPTION OF THE PREFERRED EMBODIMENTS

Figure 1:
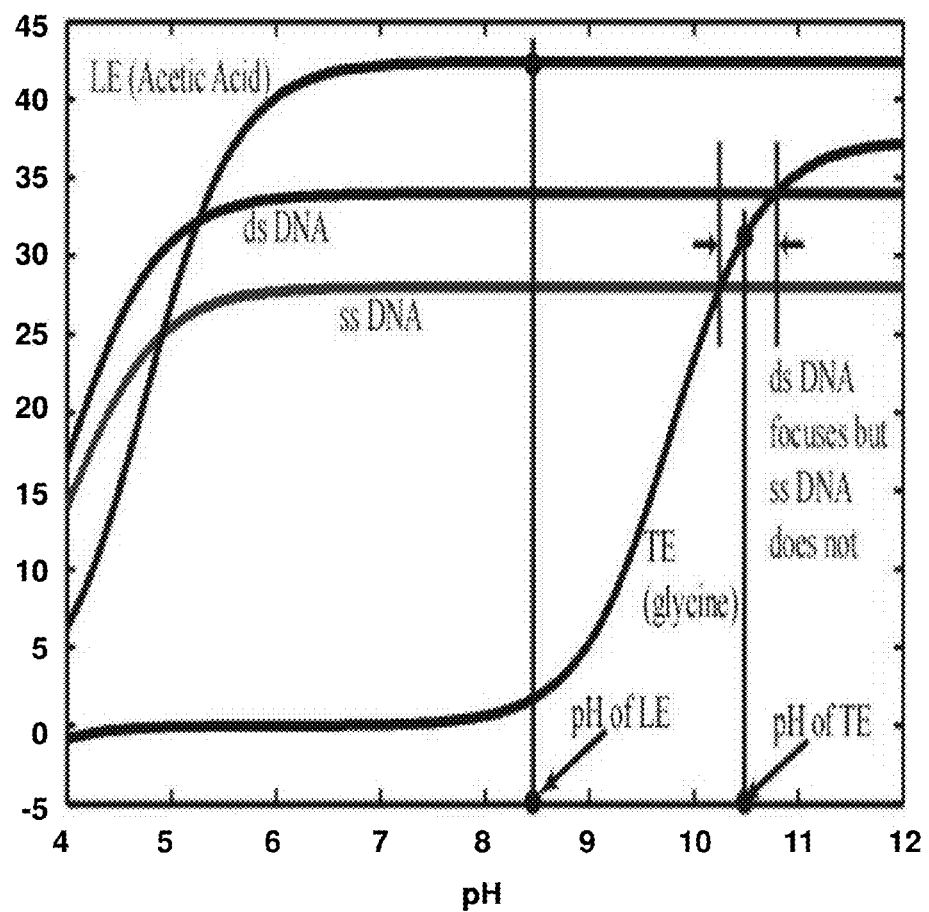
FIG. 1 is graphical representation of a buffer system and electrolytes for use in focusing double stranded DNA but not single stranded DNA. Y axis is effective mobility $\mu_{eff} 10^9$ [m$^2$ V$^{-1}$ s$^{-1}$] plotted versus pH, in acetic acid LE and glycine TE. At pH 10.5, it can be seen that dsDNA focuses but ssDNA does not.

The present description is organized as follows:
I. Overview, describing principles behind the present methods and materials;
  A. Selection of electrolyte systems
  B. Modifications 1-6;
  C. Definitions
II. Examples
  Examples 1-5—purification of nucleic acids from complex samples such as whole blood
  Examples 6-13—separation of different species of nucleic acids, especially small RNAs.
  Examples 14-16—additional modifications, suppression of electroosmotic flow, $CO_2$ aided extraction and introduction of counterions

I. Overview

The embodiments of present invention as described below can be used for fast and efficient extraction, isolation, preconcentration and quantitation of genetic material (e.g., nucleic acids) from complex biological samples based on isotachophoresis techniques. The selectivity of isotachophoretic focusing is used to concentrate nucleic acids in a sharp zone while rejecting proteins and other unwanted compounds from biological samples. The invention enables single step isolation, extraction, preconcentration and quantitation of nucleic acids from complex biological samples like blood, cell lysates, etc using isotachophoretic techniques while eliminating the need for one or more preparative steps like centrifugation or filtration. Thus, the present ITP process has been used to isolate target nucleic acids from a 'soup' of unprocessed biological samples including blood or blood lysate or cell lysates, etc.

The present methods provide high sensitivity, with a lower use of sample reagents: For example, we can currently focus less than 1 pg/µL of dsDNA. We use reservoir volumes on the order of tens of µL, and can use this to perform order 10 experiments. We can selectively extract 22-base RNA from samples also containing >200-base RNA, >100 bp DNA and proteins.

In addition, for simple fluorophores, we have demonstrated million fold preconcentration. For proteins from a complex cell-free expression buffer, we have shown 10,000-fold preconcentration in 3 min. The present ITP zones are self-stabilizing and injection protocols are easily conducted with two pipetting dispensions (e.g., in straight channels).

The present ITP preconcentration and separation assays take 10's to 100's of seconds.

The present methods can be combined with counterflow (for stationary ITP) to process large volumes (e.g., order 100 µl volumes of DNA in 30 minutes).

The following examples demonstrate that the technique isolates RNAs with lengths of roughly 22 nt (in the range of miRNAs and siRNAs), and that its selective isolation rejects 66 nt and larger RNAs. We are able to quantitate small RNAs of only ~900 cells in ~5 µL, and we believe that the sensitivity can be decreased considerably, allowing small RNA extractions from single cells. The examples also demonstrate the application of ITP for sample preparation from biological fluids for further analysis including for PCR.

Sample ions focus in a sharp zone at the interface between the trailing and leading electrolytes if their charge is of the same sign (i.e., all are either anionic or cationic) and (a) the effective mobility of the sample ions in the TE is faster than that of the TE ions This is shown by formula (1) ions:

$$|\bar{\mu}_{s,TE}| > |\bar{\mu}_{TE,TE}| \tag{1}$$

and (b) the effective mobility of the sample ions in the LE is lower than that of the LE ions. This is shown by formula (2):

$$|\bar{\mu}_{s,LE}| < |\bar{\mu}_{LE,LE}| \tag{2}$$

Subsequently, equations (1) and (2) determine focusing inequalities. The effective mobilities are defined in equation (3):

$$V = \bar{\mu} E \tag{3}$$

Where V is the average velocity of a species and E is the electric field in the corresponding zone. The overbar on the µ indicates the effective (not fully ionized) mobility of a weak electrolyte ion. The first subscript in mobility indicates the relevant chemical species ("s" for sample and "TE" for trailing ion), and the second subscript indicates the zone. $\bar{\mu}_{s,TE}$ is therefore the effective mobility of sample in the TE zone.

A. Selection of Electrolyte Systems

The present methods essentially involve selection of electrolyte systems including buffer systems and chemical mobility modifying agents, according to the above formulas, and as described in detail below. The electrolyte system may comprise a solvent (e.g., water) buffering counterions, an LE with selected ionic species, a TE with selected ionic species, and possible spacers surface-active compounds, and the like.

According to the present methods, the LE and TE are selected to have with effective mobilities, as defined above, that are higher (in LE) and lower (in TE) than that of the target nucleic acids. Upon application of an electric field, nucleic acid molecules focus between TE and LE in a sharp concentrated zone. Species with smaller effective mobilities than the TE migrate into the channel but lag behind and do not focus. Faster species overspeed the sample zone and also do not focus. As an example, at moderate pH and in free solution, DNA has relatively large magnitude (negative) mobility compared to a vast number of polypeptides, so the mobility of the TE effectively determines purification selectivity. The term "effective mobility" is equivalent to observable mobility. That is the ratio of velocity to electric field at the specific conditions. This is distinguished from "fully ionized mobility in the infinitely dilute limit" which is thought of as more of a material property.

In typical ITP, analytes at sufficiently high concentration (and after sufficient focusing time) segregate into distinct zones characterized by a plateau at steady state. The composition of plateau zones is described fairly generally by the Alberty (R. A. Alberty, *J. Am. Chem. Soc.*, 1950, 72, 2361-2367) and Jovin T. M. Jovin, *Biochemistry*, 1973, 12, 871-878) functions governing ITP electromigration dynamics. However, analytes at initially trace concentrations rarely have sufficient time (or channel length) to achieve plateau zones. Such analytes focus into approximately Gaussian peaks, and this regime is thus called peak mode ITP (S. J. Chen, S. W. Graves and M. L. Lee, J., *Microcolumn Separations*, 1999, 11, 341-345). Khurana and Santiago (T. K. Khurana and J. G. Santiago, *Anal. Chem.*, 2008, 80, 6300-6307) presented a theoretical and experimental study for the electrolyte composition optimization in the peak mode regime. We followed their theoretical guidelines in designing our ITP system chemistry. The selection of the electrolyte system is crucial since this allows us to selectively extract and isolate small NAs from a large variety of other biomolecules present in the cell lysate.

A key aspect of the present method is selection of TE that is just slower (no more) than the target NA and selection of LE that is just faster than the target NA so as to ensure high selectivity of extraction of NA from a complex biological sample. As described below, the present methods involve selection of pH, mobility conductivity and ionic strength. The LE and TE may have the same or different pH; the mobility An example of the present methods of LE, TE and buffer selection is shown in FIG. 1.

FIG. 1 shows a graphical representation, in a plot of pH versus effective mobility, of a system that selectively focuses either single- or double-stranded DNA. Plotted is a schematic representation of the effective mobility of dsDNA, ssDNA, LE, and TE as a function of pH. The values of the TE and LE pH are shown along the abscissa. Highlighted is the range where the LE and TE mobilities bound that of dsDNA but not that of ssDNA. In this zone, ss DNA has lower mobility than the TE in the TE zone, so it will not focus. Here, the LE is 2-(N-morpholino) ethanesulfonic acid (MES), and the TE is glycine.

To select a particular LE and TE, one can proceed by dichotomy: First, start with LE and TE that have a large focusing window and focus sample of interest. Then, select a new TE that cuts the previous window by half and verify focusing. Then, if sample focuses, repeat; or use a new LE that cuts the window by half and repeat. This process can be iterated until the desired selectivity (e.g., LE and TE with +/−1% of the sample mobility) is reached.

By further adjustments of reagents and effective mobilities, the present isotachophoresis methods are used for simultaneous extraction of DNA and RNA. The trailing and leading ions are selected such that DNA and RNA both focus at the TE/LE interface, that is, both DNA and RNA meet the focusing inequalities. Once the microchannel is primed with the LE solution, and upon application of an electric field in the microchannel, DNA and RNA will focus and concentrate between TE and LE. The TE and LE are chosen such that species not to be focused (e.g., lysed cell membrane, proteins, etc.) have their electrophoretic mobility either smaller than the trailing ion or larger than the leading ion. The slower species will remain in the TE well while faster species exiting the TE well overspeeds the nucleic acid zone and proceeds to the LE well. For short focus times, a finite quantity of fast species remains in the TE well. These can be removed completely given longer focusing times (e.g., via the application of counterflow). In one embodiment, it is possible to reduce the electroosmotic flow (EOF) by coating the channel walls. Such a coating can enhance the recovery of nucleic acids by reducing their adsorption on the walls.

By further adjustment of reagents and effective mobilities, ITP is used herein to selectively extract RNA and not DNA from the lysed cell sample. In this case, LE and TE mobilities are chosen such that only RNA meets the focusing inequalities, while DNA migrates through the TE/LE interface and into the leading well. This scheme assumes that the RNA mobility is less than that of DNA. If conditions are such that RNA mobility is greater than DNA, then buffers can be chosen such that RNA meets the focusing inequalities, but DNA does not.

For the latter, we need electrolytes with mobility values bounded by that of RNA and DNA. This may be accomplished by leveraging the size-dependent mobility of DNA and RNA in free solution. Alternately, we can use a sieving matrix to affect a strong size dependence on RNA and DNA.

The samples contemplated here will have a variety of molecular species. One species will be concentrated in the interface between LE and TE.

Examples of LE and TE are chloride ions as LE and 6-aminocaprroic acid as a TE; Tris+HCl as an LE and TRIS HEPES as a TE; 6-aminocaproic acid and HCl as LE and 6-aminocaproic acid and caproic acid or Bis-Tris and Dihydroxybenzoic Acid as TE; and Tris-HCl as LE and glycine or TRIS-glycine as TE. These are adjusted as to concentration and buffers to provide the effective mobility differentials as described above. Exemplary buffering counterions include: mM BisTris, pH 6.0; mM Tris, pH 7.6; 267 mM BisTris and 100 mM NaOH, pH 6.7.

B. Modifications to Selective LE/TE Buffer Components

In addition to the methods taught here for selecting the LE, TE and other components for focusing of the desired nucleic acid species, other steps can be employed for further enhancements:

(1) A sieving agent may be added in the separation channel to change mobility of the macromolecules not to be concentrated. In one aspect of the invention, small RNAs are extracted, isolated, preconcentrated and quantified from complex biological samples using ITP in microchannels loaded with a high efficiency sieving medium. An example of a sieving medium is Pluronic F-127. Pluronic F-127 is a triblock copolymer PEO-PPO-PEO, where PPO is poly (propylene oxide) and PEO is poly (ethylene oxide). At temperatures below 15° C. the viscosity of this amphiphilic copolymer solution is low because PPO is hydrophilic, and Pluronic F-127 dissolved in water acts as a free flowing solution. When the temperature is increased, the hydrogen bonds between PPO and water are broken, leading to a high degree of PPO hydrophobicity so that micelles are formed. These spherical micelles with hydrophobic PPO cores surrounded by PEO brushes are packed in a face-centered cubic nanostructure, forming a liquid crystalline phase. It was measured for 20% Pluronic F-127 that the viscosity at 4° C. is ~50 cP compared to a value of ~900 cP at 22° C. The mobility of small RNAs in this sieving matrix decreases with increasing number of nucleotides. We have searched for and found an effective mobility for our TE which is between the mobility of small RNAs and pre-miRNAs in the sieving matrix, hence separating these species. These were determined from simulations using Peakmaster 5.2 for the buffer calculations (including ionic strength dependence).

Hydrophilic polymers such as linear low-molecular-mass polyacrylamide or low molecular-weight poly(ethylene oxide) (PEO) are suitable sieving polymers.

Block copolymers comprise two or more homopolymer subunits linked by covalent bonds. The union of the homopolymer subunits may require an intermediate non-repeating subunit, known as a junction block. Block copolymers with two or three distinct blocks are called diblock copolymers and triblock copolymers, respectively. Copolymers may also be described in terms of the existence of or arrangement of branches in the polymer structure. Linear copolymers consist of a single main chain whereas branched copolymers consist of a single main chain with one or more polymeric side chains. A number of different monomers are known for use in preparing block copolymers, including isoprene and styrene.

A sieving matrix would also allow the selective focusing of DNA with any range of lengths (2) Electroosmotic flow suppression/microchannel treatment is effected by addition of a chemical agent to enhance selectivity. Examples of agents used to suppress electroosmotic flow include polylactams, such as polyvinylpyrrolidone, substituted polyacrylamide derivatives, water-soluble methylhydroxyethyl derivatives of cellulose, polyvinylalcohol, polyvinylpyrrolidones and polyethyleneglycols and non-ionic detergents like Triton X-100. In one embodiment, LE may be of high mobility, thus increasing ITP velocity and decreasing the detection time.

The microfluidic channels may be treated for electroosmotic flow suppression or for other beneficial flow modifying effects. The microchannels may be of a non-conducting material like silicate or borosilicate. The microchannels may be pretreated with one or more agents including silanizing agents, alcohols, acids and water. The microchannels may be present in a simple cross geometry, that is, they may be branched at one end, as illustrated, or may be in a comb configuration, with several branches.

Polyvinylpyrrolidone, formula $(C_6H_9NO)_n$, CAS 9003-39-8, and may be the lower molecular weight form, about 40,000 or the higher form, about 360,000.

(3) Sample disruptive or degradative agents are used to treat a complex biological sample. These agents are those for lysing cells in a whole blood or other cell-containing sample, degrading proteins or lipids in a sample, or the like. Examples of lysis agents include detergents and surfactants, preferably non-ionic surfactants. Examples of non-ionic surfactants include Triton-X-100 and Igepal CA-630. In one embodiment, the lysis buffer may not include chaotropic agents. In one embodiment, a nuclease (DNAse or RNAse) or a nuclease inhibitor may be added to the lysis buffer to ensure selectivity of the nucleic acid being purified (DNA or RNA). In another embodiment, a protease enzyme like Proteinase K is added to the lysis buffer.

A proteinase, also known as a protease, is an enzyme that breaks down proteins by hydrolyzing peptide bonds. Protease enzymes (like Proteinase K) may be used to degrade proteins which potentially inhibit PCR into short polypeptides. However, proteinase K is itself a PCR inhibitor. We compensate for this by operating with an ITP chemistry where proteinase K (pI=8.9) is positively charged and is, therefore, kept away from the sample zone as it electromigrates in the opposite direction (enters and remains in the TE reservoir). The combination of proteinase K and ITP-based purification effectively removes PCR inhibiting species and other polypeptides from the biological sample. During purification, the biological sample is hydrodynamically injected between LE and TE. Upon application of an electric field, nucleic acids focus and migrate towards the anode in a sharp concentrated zone. When the focused nucleic acids enter the anode reservoir, they are pipetted out (in a very small volume up to 5 µl), added to a PCR mix and real time PCR is performed.

In one embodiment, a single mixture of lysing agent and TE is added to the sample and ITP is performed for separation and concentration of nucleic acids. The single mixture serves two functions: lysing cells in the sample as well as being the trailing electrolyte for focusing the nucleic acids in the sample.

The location of the focused nucleic acid ITP zone may be tracked by monitoring ionic current or by fluorescence visualization. Fluorescence dyes like SYBR Green are used to intercalate between nucleic acids to facilitate detection of the purified nucleic acids. Inverted epifluorescence microscopes may be used to detect the isolated and purified nucleic acids. Images are captured on a CCD camera. Standard and ITP-focused images are corrected with the background and their ratio obtained. An integrated normalized intensity of the nucleic acid is calculated and then converted to nucleic acid mass. Calculations may be done using standard software packages like MATLAB (The Mathworks, Natick, Mass.).

(4) Counterions may be used to tune the mobilities of the LE and TE.

Selective focusing of nucleic acids may be enhanced with multiple counterions to independently tune the effective mobilities of the TE and LE. In conventional ITP, the effective mobility of the TE is coupled to that of the LE because the pH of the LE has a strong influence on the pH of the TE and sample regions. pH largely determines the effective mobility of the species. In embodiments of the present invention, the relation between the pH of the TE and the pH of the LE is changed substantially by adding a second counterion to the LE to modify the pH of the TE (while the pH of the LE remains approximately constant). By largely independently tuning the effective mobilities of the LE and the TE, very precise, fast, and efficient separation of the sample is possible. Since pH largely determines the effective mobility of a species, this method uncouples the effective mobilities of the two electrolytes.

A dual ion process described here can be used in a real-time adjustment of chemistry performed with a microchip with two LE wells as described in Example 16 below.

(5) Carbon dioxide e.g., from the atmosphere, may be used to achieve ITP which simultaneously preconcentrates and separates analyte species. Since the wells are open to atmosphere, carbon dioxide continually reacts and enters the channel. $CO_2$ reacts with water to form a carbonate zone. A carbamate zone forms directly from the reaction of dissolved $CO_2$ with primary and secondary amines present in the solution. With appropriate LE and TE chemistries, these carbonate and carbamate zones focus and also create electric field gradient region between the LE and TE boundaries. The analytes focus in this gradient region based on their electrophoretic mobility and we achieve simultaneous focusing and separation of these analytes. Analytes separated include nucleic acids from a complex biological sample or one or more proteins from a complex biological sample.

(6) Counterflow of the bulk liquid may be used to increase the focusing time and the amount of focused material. The counterflow (of the solvent) is applied in the opposite direction of ITP electromigration. This counter flow can be achieved using either a pressure gradient to create pressure-driven flow, or by taking advantage of the electroosmotic flow (e.g., as in the case of the electrophoresis of anions in a channel with a negative wall surface charge). The counter flow of the background liquid in the direction opposite of the electromigration will slow down the sample and therefore increase its residence time within the capillary. Increased residence time allows for preconcentration of trace analytes from relatively large volumes into small, recoverable sample volumes. In addition to long term stacking, the process also allows larger separation times of ionic species by isotachophoresis.

C. Definitions

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. Generally, nomenclatures utilized in connection with, and techniques of, cell and molecular biology and chemistry are those well known and commonly used in the art. Certain experimental techniques, not specifically defined, are generally performed according to conventional methods well known in the art and as described in various general and more specific references that are cited and discussed throughout the present specification. For purposes of the clarity, following terms are defined below.

The terms "isotachophoresis," ITP, or isotachophoretic, is used in its conventional sense, and refers to a nonlinear electrophoretic technique used in the separation of a variety of ionic compounds, as described in detail below. Unlike "linear" zone electrophoresis in which separating solute bands continually spread by diffusion or dispersion, ITP forms self-sharpening, adjacent zones of substantially pure solute. Sample is usually introduced between the leading electrolyte (LE, containing leading ion) and the terminating electrolyte (TE, containing terminating ion) where the leading ion, the terminating ion and the sample components must have the same charge polarity, and the sample ions must have lower electrophoretic mobilities than the leading ion but larger than the terminating ion. After application of a fixed electric current, sample components move forward behind the leading ion and in front of the terminating ion and form discrete, contiguous zones in order of their electrophoretic mobilities. Then, following a brief transient period where the discrete solute zones are formed, this ITP "stack" assumes a fixed concentration profile with a constant velocity moving in the direction of the leader. ITP differs from capillary electrophoresis in that it uses a discontinuous buffer system as described above. Also, capillary electrophoresis is characterized by the use of high voltages, which may generate electroosmotic and electrophoretic flow of buffer solutions and ionic species, respectively, within the capillary. The properties of the separation and the ensuing electropherogram have characteristics resembling a cross between traditional polyacrylamide gel electrophoresis (PAGE) and modern high performance liquid chromatography (HPLC).

The term "nucleic acids" or "polynucleic acids" refers to polymeric or oligomeric strands of DNA or RNA. RNAs include small RNAs such as siRNAs, miRNAs and piRNAs. siRNAs are generated from double-stranded RNAs (dsRNAs) which are cleaved to ~21-25 nucleotides (nt) by Dicer, an endonuclease belonging to the RNaseIII family serving as a molecular ruler. By contrast, miRNAs are derived in a two-step process. The primary precursors of miRNAs (pri-miRNAs) are encoded in the genome, having lengths of several hundred to thousands of nucleotides. In animals, the pri-miRNAs are then processed to ~70 nt pre-miRNAs which are transported into the cytoplasm, where the pre-miRNAs are cleaved to produce mature ~21-25 nt miRNA-iRNA*duplexes (where miRNA is the antisense, or guide, strand, and miRNA* is the sense, or passenger, strand). Biogenesis of the third class, piRNAs which are single-stranded RNAs (ssRNAs) and ~24-31 nt long, is distinct from that of siRNAs and miRNAs and does not involve dsRNA precursors.

The term "microfluidic device" is used in its conventional sense to refer to a device which is typically on a chip, for carrying out fluid manipulation, "on chip." The device contains a sample well and microchannels is that the depth dimensions of etched channels (typically 10-20 µm deep). A sample is introduced into the microchannel system using various electrokinetic—or pressure—injection methods. U.S. Pat. No. 6,695,009, whose contents are incorporated by reference to the extent necessary to understand the present invention, shows one prior art approach to sample stacking. Further description of an exemplary microfluidic device may be found in Santiago et al. US 2006/0042948 A1, entitled "Microfluidic Electrophoresis Chip Having Flow-Retarding Structure." A flow retarding structure is not required for present purposes. The present microchannels may also be capillary tubes, which are generally about ½ mm in internal diameter. Channel areas may be, e.g., 1000-5000 µm$^2$.

The term "electroosmotic flow" refers to the motion of liquid induced by an applied potential across a porous material, capillary tube, microchannel, or other fluid conduit. Because electroosmotic velocities can be independent of conduit size, whereas flow due to pressure gradients is much more significant with large conduits, electroosmotic flow is most important when the fluid conduit is small. Electroosmotic flow is an essential component in certain chemical separation techniques, notably capillary electrophoresis.

II. Examples

Figure 2A:
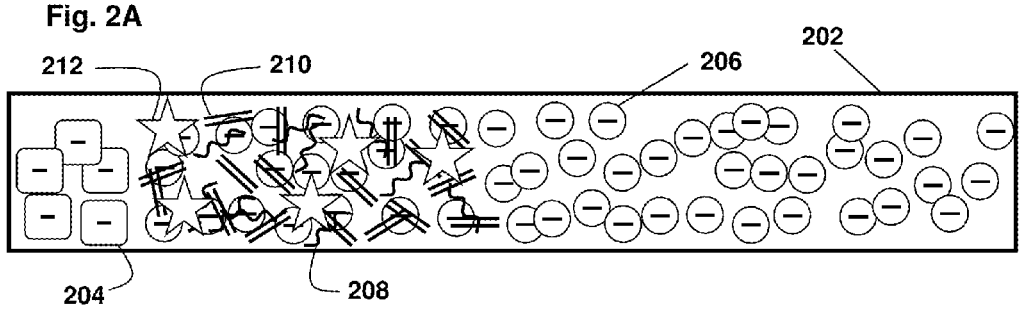
FIGS. 2A, 2B, and 2C are a schematic representation of the ITP-based nucleic acid purification from a complex biological sample showing a complex sample (2A), sample beginning to separate as V is applied (2B), and concentrated sample between LE and TE (2C).
Figure 2B:
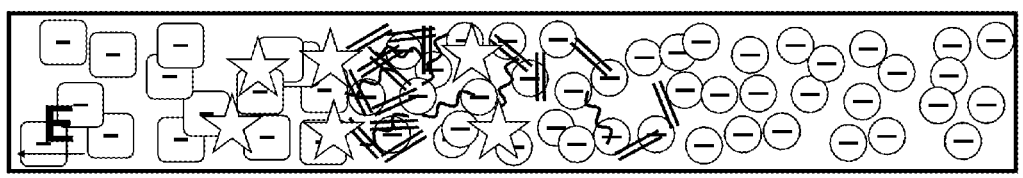
Figure 2C:
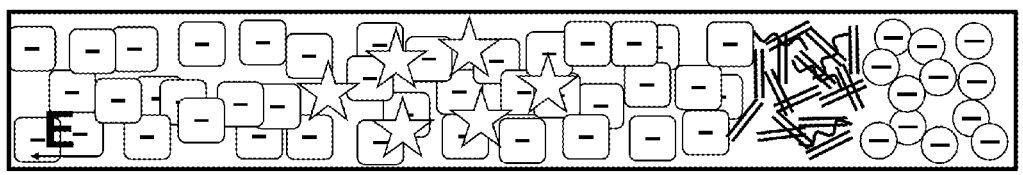

Example 1: Purification of Nucleic Acids from Whole Blood Using Isotachophoresis As shown in FIG. 2A-C, the present principles of nucleic acid purification from complex samples involve the use of an LE (circles 206) and TE (squares 204) in a microchannel 202. The sample initially comprises a plug of mixed components, shown as DNA (double lines 210), RNA (curved lines 208) (collectively "NA") and proteins and other content (stars 212). In the middle panel FIG. 2B, the initial separation of nucleic acids by moving in to the LE is shown. In the bottom panel FIG. 2C, the NA are shown between the LE and TE, while other components remain in the TE. That is, LE and TE are selected with mobilities, respectively, larger and smaller than NA. The TE needs to have larger mobility than proteins (and other contents) present in blood lysate. We inject a finite plug of lysate between TE and LE. Upon application of an electric field, NA focus between LE and TE, while proteins cannot focus as they travel slower than the ITP interface. After sufficient time, the ITP zone contains only pure NA extracted from the lysate.

Figure 3:
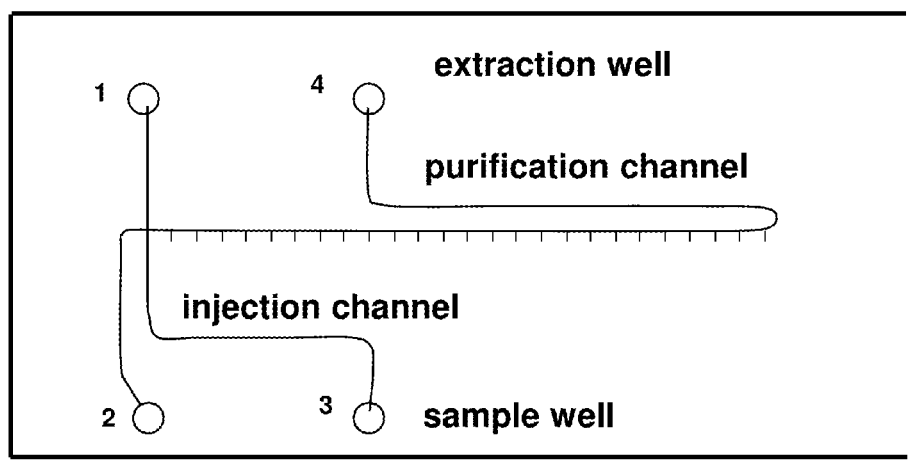
FIG. 3 is a schematic of a design of a microfluidic chip used to perform ITP-based purification of nucleic acids.

The design of the microchip used in these experiments is shown in FIG. 3. FIG. 3 shows a microfluidic chip which has four wells, with two channels terminating in wells 1 and 3 and 2 and 4, respectively. The channel between wells 1 and 3 provides an injection channel. This crosses a purification channel between wells 2 and 4 (the extraction well). Sample is injected from reservoir 3 by applying a vacuum at 2. Typically all four channels and reservoirs were filled with LE. Reservoir 3 is emptied with a vacuum and as little as 1 µL of sample is added into that reservoir. Then a vacuum is applied to reservoir 2 to fill the injection channel with the sample. We carefully removed the sample remaining in reservoir 3 and then rinsed and replaced it with TE. We then immediately applied an electric field between 3 and 4 (0-3000 V) with a sourcemeter (model 2410, Keithley, Ohio) to carry out the purification. We used the current signal to locate the ITP interface in the channel, as described further below in connection with Example 3.

Microchip Preparation:

We performed on-chip experiments in a microchip with 90 μm wide by 20 μm deep borosilicate microchannels in a simple cross geometry (FIG. 7A, 7B, 7C) (model NS12A, Caliper Life Sciences, CA).

We treated the channels with the silanizing agent Sigmacote (Sigma, MO) as follows. We first rinsed the channel 10 min with a 1:1 methanol/hydrochloric acid solution, followed by 10 min of concentrated sulfuric acid. We then rinsed the channels with deionized water for 2 min or more and dried them thoroughly with a vacuum. Next, we applied the silanizing solution for about 10 min. We then rinsed the channels with hexane and deionized water. To avoid cross contamination, we rinsed the chip between each experiment as follows: 2 min with a 1:10 (v/v) household bleach solution (Clorox, CA), 2 min with deionized water, and 2 min with leading electrolyte buffer (see below).

Sample Lysis:

Blood samples from a healthy donor were collected in heparin tubes and stored in 2 mL aliquots at −80° C. Before each set of experiments, we thawed one blood aliquot and prepared a stock of lysis buffer containing 1% Triton X-100 (Sigma, MO) in 50 mM Tris hydrochloride at pH) 8.2. We diluted 10 μL of whole blood and 4 μL of proteinase K (RNA grade, Invitrogen, CA) in 86 μL of lysis buffer. We then incubated the lysate 10 min at 56° C. in a hot bath. In the case of the second control in FIG. 4B (third bar in the plot), we added 4 U of deoxyribonuclease I (DNase I, amplification grade, Invitrogen, CA) to the lysate and incubated for 15 min at room temperature prior to proteinase K treatment. To quantify the ITP extraction efficiency, we diluted a commercial standard solution of λ-DNA (0.333 mg mL-1, Invitrogen, CA) in lysis buffer and used this as a standard sample. All solutions were prepared with DNase/RNase free deionized water (Gibco, CA).

Isotachophoresis-Based Purification:

Leading (LE) and trailing electrolytes (TE) were, respectively, 50 mM Tris titrated with hydrochloric acid to pH) 8.2 and 50 mM Tris titrated with HEPES to pH=7.8. LE and TE each contained 1×SYBR Green I (Invitrogen, CA) for fluorescence visualization and on-chip DNA quantitation. We obtained the best results adding also 0.1% Triton X-100 to reduce electroosmotic flow and protein adsorption (in conjunction with silanization treatment). For each experiment, we first filled all four channels and reservoirs with LE. We emptied reservoir 3 with a vacuum and pipetted 1 μL of lysate into that reservoir. We then applied a vacuum to reservoir 2 to fill the injection channel with lysate (~25 nL). We carefully removed the lysate remaining in reservoir 3 and then rinsed and replaced it with TE. We then immediately applied an electric field between 3 and 4 (500 V) with a sourcemeter (model 2410, Keithley, Ohio) to carry out the purification. We used the current signal to locate the ITP interface in the channel (see below, Example 4). We used this same injection protocol for the extraction efficiency quantitations performed with λ-DNA.

Visualization:

We performed on-chip visualization on an inverted epifluorescent microscope equipped with a 4×(Plan APO, N.A.=0.2, Nikon, Japan) or a 10× objective (Plan APO, N.A.=0.45); a mercury light source (Ushio, Japan); a filter cube (exciter/emitter 485/535 nm, Omega, VT); and a 0.6× demagnification lens (model RD060-CMT, Diagnostic Instruments, MI). We acquired images with a CCD camera (Cascade 512F, Roper Scientific).

On-Chip Quantitation:

We quantified the amount of DNA extracted from whole blood by first calibrating our fluorescence measurement. For the calibration, we used a control solution of genomic DNA purified from blood with the DNeasy blood and tissue purification kit (QIAGEN, CA). We measured its DNA concentration with a Nanodrop 1000 spectrophotometer (ThermoScientific, MA) and prepared a 1.42 μg mL-1 standard solution stained with 1×SYBR Green I in LE. We acquired images of the fluorescent profile of this standard filling the purification channel (but without performing ITP). Using these images, we were able to relate peak areas to DNA mass in the ITP experiments. Raw data I for a DNA ITP zone from a DNA purification experiment from blood lysate can be imaged as a band. The fluorescence profile $I_{std}$ of the channel filled with the standard DNA solution (here 1.42 $\mu g \cdot mL^{-1}$ of human genomic DNA) can also be determined. Also, the background fluorescence $I_{bgd}$, where the channel is filled with deionized water. We correct both ITP-focused DNA and standard images with the background, and then take their ratio. This yields an image where the value of each pixel is in units of standard. Summing over all pixel yields the integrated, normalized intensity F in terms of these standard units. To convert this number to DNA mass, we take its product with the standard concentration and the volume of each pixel (pixel area times the channel depth, assuming an approximately rectangular channel cross section). We performed all calculations using MATLAB (The Mathworks, MA). We also performed this calibration with a solution of λ-DNA.

The following formula was used:

$$F = \sum^{all\ pixels} \frac{I - Ibgd}{Istd - Ibgd}$$

Where I is intensity and a standard solution is compared against background.

Focused DNA mass=$F \times p_{std} \times V_{pixel}$ $P_{std}$=concentration of standard solution (pg/nL)

Vpixel=pixel volume

=pixel width×pixel height×channel depth.

Referring again to FIG. 4B, the bars show mean values of NA mass purified from blood lysate, as calculated from the fluorescence intensity profile described above. Purifications of DNA from about 2.5 nL of whole blood (25 nL of blood lysate) provided results from three sets of experiments: purified blood lysate, blood lysate treated with proteinase K, and blood lysate treated first with DNase and then proteinase K. We used SYBR Green I fluorescence measurements to estimate the amount of DNA recovered in the ITP zone (see above, Example 1). The amount of DNA recovered without proteinase K is negligible (on the same order as the negative control). The mass of focused DNA is significant when performing the assay on a lysate initially treated with proteinase K. The third set of results shows ITP purification of a lysate treated with DNase prior to proteinase K treatment. This control case shows low DNA recovery, as expected. We hypothesize that DNA binding proteins (in particular histones) significantly reduce the electrophoretic mobility of DNA by increasing the hydrodynamic Stokes' drag of the complex. If the mobility of the DNA-protein complex is smaller than the mobility of the TE, DNA does not focus and cannot be purified. Proteinase K releases DNA from binding proteins allowing focusing and purification. Together, these experiments show that our fluorescence signal is due to focused DNA from the lysate samples and that the extraction process is suitably repeatable. We show an image of ITP-focused DNA zone above the bar graph. The amount of focused DNA is 44.2±6.2 pg. We injected 2.5 nL of blood, which contains between 65 and 162 pg of DNA. A nanoliter of blood from a healthy human contains 4-10 white blood cells, and each human diploid cell contains about 6.6 pg of DNA so that our purification efficiency for a blood sample ranges between 30% and 70%, which competes with both batch and microchip-based SPE methods. Uncertainty bars represent uncertainty in measured mass of DNA with a 95% confidence interval. The three sets are results from N=2, 9, and 2 repetitions, respectively.

Example 2: Characterization of Extraction Efficiency of Purified DNA Produced

In purification procedure for DNA, there are at least two extraction efficiencies of interest: the fraction of DNA purified and focused via ITP from the amount injected into the channel and the amount of DNA extracted from the chip and delivered to PCR versus the amount of DNA in the lysate dispensed into the chip. To characterize the former, we applied our technique to a solution of λ-DNA of known concentration. We injected 10 pg of λ-DNA on-chip and performed the ITP purification as described in Example 1. We determined the amount of focused DNA by quantifying SYBR Green I fluorescence and comparing it to the standard. We measured the mean fraction of extracted DNA (v. amount injected into the channel) as 1.03±0.06 (N=3). This approximately complete extraction is at least as good as traditional extraction methods (e.g., QIAGEN kits) and state-of-the-art microsolid phase extraction devices 6. We estimate that we extract out of the chip (and deliver to the PCR) approximately all of the DNA which we focus on the chip.

Example 3: Localization and Extraction of ITP-Purified DNA

Figure 5A:
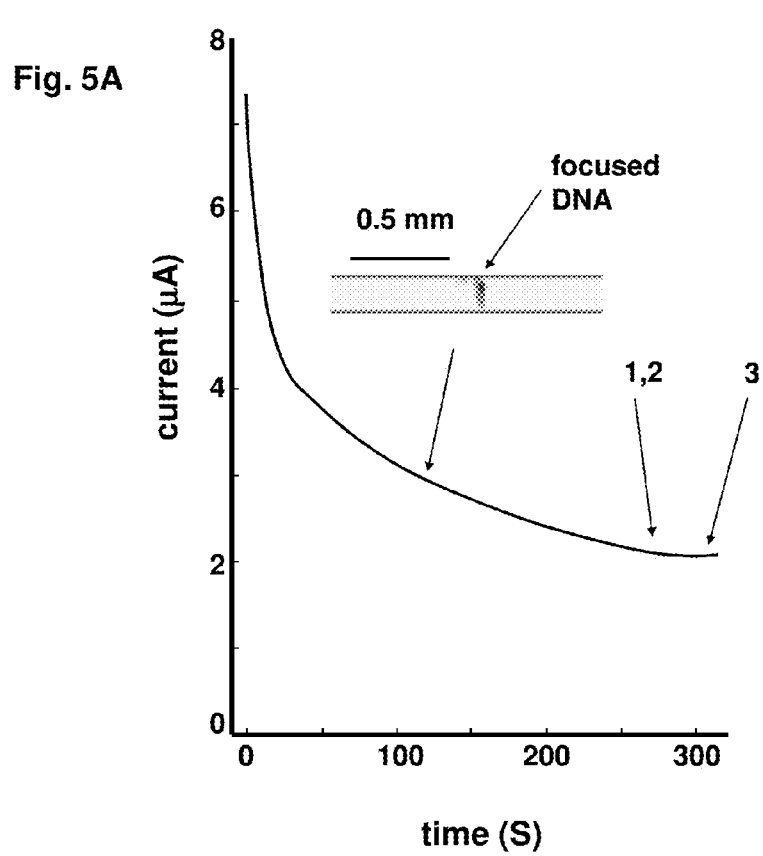
FIGS. 5A and 5B are a graph and a diagram, respectively, illustrating localization and extraction of ITP purified nucleic acids.
Figure 5B:
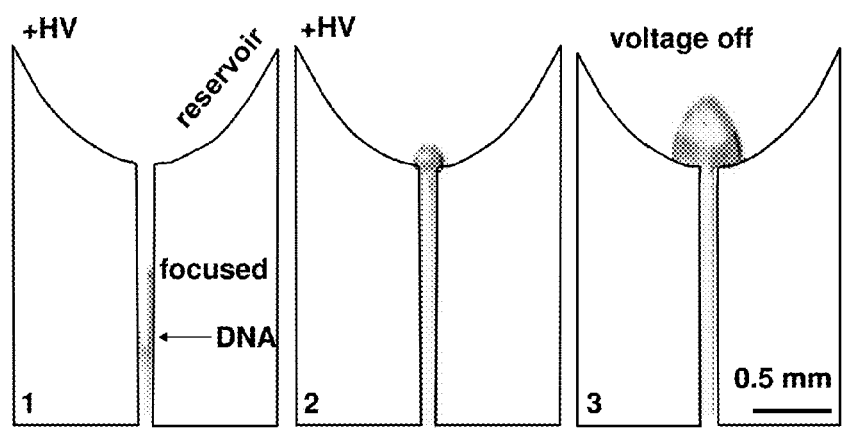

We track the location of the focused NA ITP zone by either monitoring ionic current or by fluorescence visualization. FIG. 5 shows a measured current trace obtained from a constant voltage ITP extraction experiment where the sample is a solution containing 7 ng.; L-1 of lambda λ-DNA. We acquired the current trace by interfacing the sourcemeter with MATLAB using a GPIB card (National Instruments, TX). The current decreases monotonically as the ITP interface advances within the channel, as the relatively low conductivity TE replaces the high conductivity LE. At the moment where the current reaches a plateau (here near t=260 s), the purification channel is entirely filled with TE and the ITP interface has reached the anode reservoir. Above the current plot (5A), is an actual image of focused DNA in the microchannel (with a superposed schematic of walls). FIG. 5B shows drawings of actual fluorescence images corresponding to the same experiment. Image 1 shows the focused DNA approaching the reservoir. Image 2 shows an image of the same location just after the interface enters the reservoir. Image 3 shows the reservoir about 20 s later, where the purified NA has migrated into the reservoir. These three instances in time are highlighted in the current plot. Either or both current monitoring and fluorescence visualization can be used to track the position of the NA during the purification process.

Example 4: Off-Chip PCR of Purified DNA

We tracked the position of the focused zone in the channel by directly visualizing the focused species or by monitoring current transients (see above, Example 3). After the ITP interface exited the purification channel, we collected the liquid from reservoir 4 (~2 µL) with a standard pipettor into a PCR tube containing 5 µL of 2×Fast SYBR Green I master mix (Applied Biosystems, CA) and 0.1 µM primers (Invitrogen, CA) targeting a 201 bp fragment of the BRCA2 gene and filled the rest of the reaction tube with deionized water up to 10 µL.

The primer sequences for the BRCA2 201 bp fragment amplification are the following:
Forward primer: CAC CTT GTG ATG TTA GTT TGG A (SEQ ID NO: 1)
Reverse primer: TGG AAA AGA CTT GCT TGG TAC T (SEQ ID NO: 2)

The procedure may be summarized as follows: At $t_0$, the lysate is injected and is concentrated near the TE well, interfacing with the LE. As time passes, the focused NA move in to the LE and through the purification channel, becoming further concentrated, until at the end time they are a narrow band at the LE end, where they are collected in a sample tube and diluted up to 10 µL. The material is pipetted from the well and processed further, in this case it can be successfully amplified by PCR, meaning that the sample does not contain materials that interfere with PCR, as by blocking enzymatic activity or DNA hybridization. All PCR reactions were prepared in a UV-sterilized fume hood to avoid contamination and allow sensitive amplification without false positives. We performed off-chip real-time PCR on an ABI 7500 Fast thermocycler with the following thermal profile: 20 s initial hold at 95° C. and 40 cycles composed of 3 s denaturation at 95° C. followed by 30 s annealing and extension at 60° C. We performed post-PCR dissociation curve analyses on the same instrument.

Example 5: Real-Time PCR Amplification of ITP-Purified DNA from Human Blood

Figure 6:
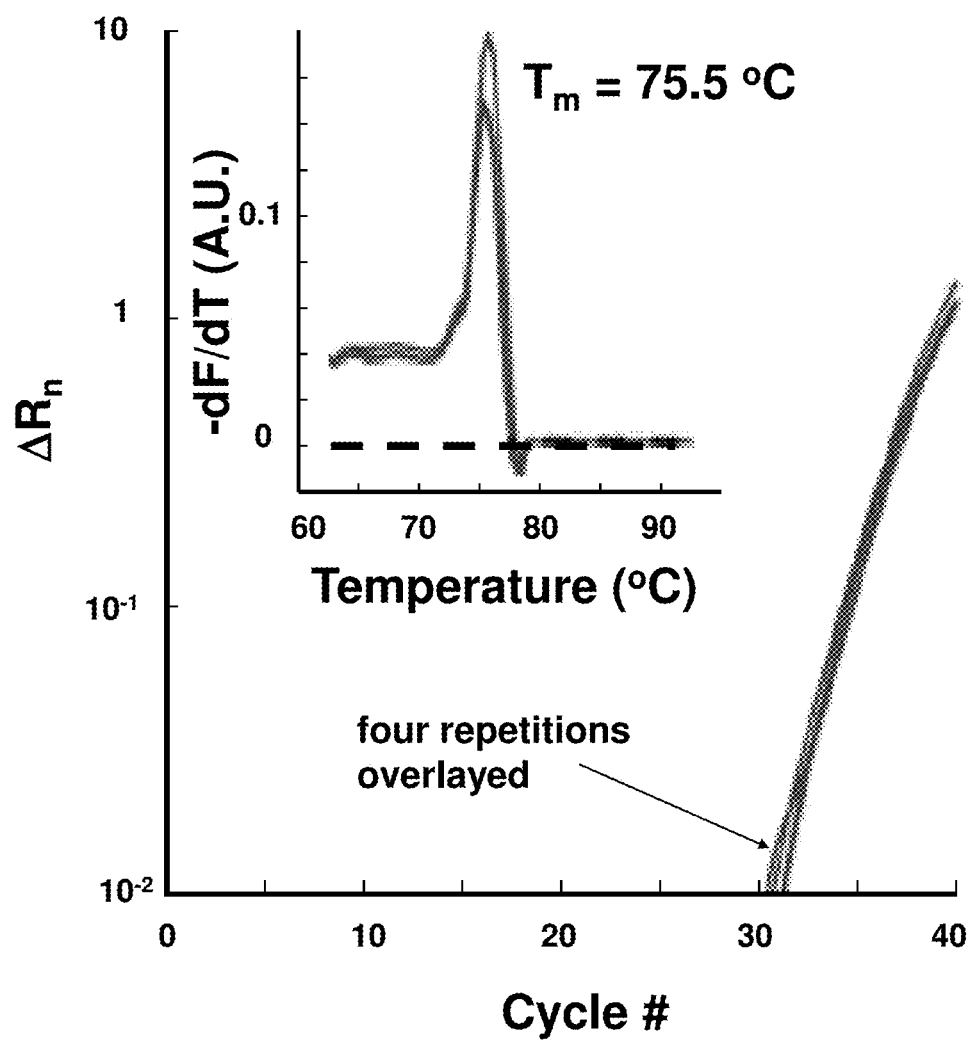
FIG. 6 is a graph showing real time PCR amplification of ITP purified DNA from human blood.

FIG. 6 shows the results of real time PCR amplification of ITP purified DNA from human blood. The amplification curve shows repeatable amplification of the extraction product (here four repetitions, threshold cycle $C_t$=30.9±0.4). Negative controls and PCR from equivalent amount of lysate showed no amplification after 40 cycles. We, therefore, successfully purified DNA from whole blood to obtain PCR-ready NA in a PCR-friendly buffer. The inset shows the post-PCR dissociation curve (derivative of SYBR Green I fluorescence). The melting temperature of the PCR product equals that of the positive control ($T_m$=75.5° C., see dissociation curves on the inset of FIG. 6). The dashed line corresponds to melting curves of negative controls. The experiment showed that we successfully and reproducibly purified DNA from whole blood and recovered genomic DNA free of PCR inhibitors.

Example 6: Selective Extraction, of Small RNAs from Cell Lysate Using On-Chip Isotachophoresis and Sieving Agent Chemicals and reagents: 6-aminocaproic acid, caproic acid, Tris, Bis-Tris, HEPES, Pluronic F-127 (registered trademark of BASF), Igepal CA-630, and sodium chloride were purchased from Sigma-Aldrich (St. Louis, Mo.). HCl and magnesium chloride hexahydrate were from EMD Chemicals (Gibbstown, N.J.). 22 nt and 66 nt oligos (both mixed base A, C, G) were from Integrated DNA Technologies (Coralville, Iowa). SYBR Green I and II; 50 base pairs (bp), 123 bp, and 250 bp DNA ladders; 0.1-2 kb RNA ladder;

293A cell line; streptavidin (Alexa Fluor 488 conjugate); albumin from bovine serum (BSA, Alexa Fluor 488 conjugate); and ultrapure DNase/RNase-free distilled water were purchased from Invitrogen (Carlsbad, Calif.). The 10 bp DNA ladder was from Promega (Madison, Wis.). We purchased embryonic kidney (293) total RNA, RNase inhibitor, and RNaseZap wipes from Ambion (Austin, Tex.).

Cell Lysate Preparation:

Cell lysing was preformed off-chip according to a standard procedure. We followed the first three steps of the RNeasy Mini Kit supplementary protocol from QIAGEN (Hilden, Germany). First, $3\times10^6$ 293A cells were pelleted by centrifuging for 5 min at 300 g and the supernatant was removed by aspiration. Second, the cells were resuspended in 175 µL of precooled (4° C.) lysis buffer and incubated for 5 min on ice. The lysis buffer contained 50 mM Tris and 30 mM HCl (pH 8), 140 mM NaCl, 1.5 mM $MgCl_2$, 0.5% (v/v) Igepal CA-630 which is a nonionic detergent, and just before use, we added 1 Uµl-1 RNase inhibitor. Third, we centrifuged the cell lysate at 4° C. for 2 min at 300 g and recovered the supernatant which contained the cell lysate.

Electrolyte Composition:

We experimented with and evaluated the performance of over 100 ITP buffer combinations (in free solution and with a sieving matrix) and several labeling techniques. Here, we describe our experiments with the best performing chemistry. We used an LE with a high mobility, 140 mM 6-aminocaproic acid and 100 mM HCl (pH 4). This LE has a high mobility compared to the TE, increasing the ITP velocity and therewith decreasing the detection time. The TE was 10 mM 6-aminocaproic acid and 50 mM caproic acid (pH 4), which mobility allows the separation of small RNAs and premiRNAs. The electrolyte system has been designed to be at pH 4, at which value most proteins contained in the cell lysate are positively charged since they have a pI>4.26 Thus, most proteins do not migrate through the microchannel and remain in the sample reservoir. We verified the latter with a set of preliminary experiments using streptavidin and albumin from bovine serum (each labeled with Alexa Fluor 488).

The pH values of the electrolytes were measured with Corning Pinnacle 542 pH/conductivity meter from Nova Analytics (Woburn, Mass.). All buffers were prepared with distilled, ultrapure, 0.1 micron filtered, RNase and DNase free water, and contained the intercalating dye 1×SYBR Green I (for dsDNA) or II (for RNA). For the experiments with lysed 293A cells we worked at concentrations of 100×SYBR Green I and II. These intercalating dyes are positively charged when they are free in solution, and so conveniently do not focus in our anionic ITP experiments. SYBR Green I and II have a much lower fluorescence quantum yield when free in solution than when complexed with either dsDNA or RNA. 27. These dyes are used effectively in a variety of analytical and diagnostic applications for the detection of nucleic acids.

Sieving Matrix:

For the separation of 22 nt from 66 nt oligos we chose Pluronic F-127 at a concentration of 30% (w/v), which has demonstrated to be highly effective for the sieving of oligos with lengths of 8-32 nt. 17,29 The triblock copolymer was dissolved in the LE and placed in the refrigerator (4° C.) for a few days prior use to ensure complete dissolution of the powder.

Imaging:

For imaging we used the inverted epifluorescent microscope IX70 from Olympus (Hauppauge, N.Y.), equipped with a 100 W mercury lamp, a 10×UPlanFl objective (NA 0.3), and XF115-2 filtercube (455-490 nm excitation, 510 nm emission, 505 nm cutoff dichroic) from Omega Optical (Brattleboro, Vt.). Images were captured with a MicroMax 1300 CCD camera controlled with WinView32, both from Princeton Instruments (Trenton, N.J.). For image analysis we used ImageJ from the National Institutes of Health and MATLAB from MathWorks (Natick, Mass.).

On-Chip Isotachophoresis Experiments:

We performed all experiments on NS-95 glass microchips from Caliper (Mountain View, Calif.), having a simple-cross geometry with wet-etched 12 µm deep by 34 µm wide channels. FIG. 7A, 7B, 7C shows a schematic of chip and experimental steps.

FIG. 7A shows filling of the microchannel with matrix; FIG. 7B shows the positions of the reagents after 10 min at about 22 deg. C. FIG. 7C shows ITP focusing of small RNAs between the LE and the TE as the material moves towards the anode. Overall, there is illustrated a schematic of the microchip and protocol for loading of the high efficiency sieving medium and extracting, isolating, preconcentrating and quantitating small RNAs using ITP. The microchip is first placed in the freezer for a period of time. Then, the north and south reservoirs are filled with LE, and the west well with the sieving medium. (a) For filling the microchannels with solutions, a vacuum is applied at the east reservoir, and immediately thereafter the west well is cleaned and refilled with LE. (b) After a warm-up period, the sieving medium transitions into a high-viscosity solution, and the west reservoir is filled with TE and small RNAs. (c) The separation and focusing of small RNAs is initiated by applying the anode in the east well and the cathode in the west reservoir. The ITP zone travels at constant velocity v downstream (iso-tacho). Small RNAs are detected just to the left of the intersection.

The separation channel from the west well to the cross has a length of 27.5 mm. For loading the separation channel with Pluronic F-127 the chip was placed in the freezer (−10° C.) for 10 min. We then loaded the north and south reservoirs with LE buffer and the west well with refrigerated Pluronic F-127 solution (T≈4° C.), and applied a vacuum at the east reservoir for 2 min (FIG. 7A). Since the resistance of the north and south channels is much lower than that of the west channel, the Pluronic F-127 sieving matrix effectively only fills the west channel. The east channel is filled primarily with LE. (Some small amount of Pluronic F-127 is drawn into the east as thin stream, but this Pluronic F-127 "fiber" was negligibly small and often not detectable.) After vacuum-assisted channel loading the remaining sieving solution was removed from the west well by aspiration with a pipette tip and vacuum line, and refilled with LE to guarantee repeatable results. We let the system warm up to room temperature for 10 min, during which period Pluronic F-127 formed a crystalline phase. After the warm-up period, we performed a pre-run at electric field strength of 200 V $cm^{-1}$ to stabilize the sieving matrix. For the application of the electric field we used the LabVIEW-controlled high-voltage power supply Microfluidic Tool Kit from Micralyne (Edmonton, AB, Canada) and placed platinum wires in the east and west reservoirs. Then, the LE in the west well was replaced by a mixture of TE and sample (FIG. 7B), and the electric field of 400 V cm-1 was applied in east-west direction. As shown in FIG. 7C, the sample zone is focused between the LE and TE and travels at constant velocity downstream, increasing in concentration and amount of sample with time as the ITP is in peak mode. Fluorescence signals were collected at the end of the separation channel just to the left of the cross. After each experiment Pluronic F-127 was removed from the separation channel by refrigerating the device and applying a vacuum at the west reservoir for a few minutes. Then, we cleaned the device with 0.1 M KOH for 15 min and thereafter with distilled, ultrapure water. Additionally, when working with 293 total RNA or 293A cell lysate, we cleaned all surfaces with RNaseZap wipes to ensure an RNase-free environment.

Transient Isotachophoresis:

The sieving efficiency of Pluronic F-127 was investigated and demonstrated using transient ITP (tITP). tITP first preconcentrates samples in a preliminary ITP step. The ITP step is then interrupted by injecting LE ions behind the TE region, and this initiates electrophoretic separation of analytes. We used a tITP protocol similar to that described by Bharadwaj et al. (R. Bharadwaj, D. E. Huber, T. Khurana and J. G. Santiago, in Handbook of Capillary and Microchip Electrophoresis and 105 Associated Microtechniques, ed. J. P. Landers, CRC Press, $3^{rd}$ edn., 2008, ch. 38, pp. 1085-1120). To load the sieving matrix we followed the same procedure as described in FIG. 7A-C, but for tITP experiments the TE was 10 mM Bis-Tris and 50 mM HEPES (pH 5.4). This TE has a lower mobility than that for the other ITP experiments, hence also focusing relatively low mobility species such as long nucleic acids, for example. After a few seconds of ITP preconcentration we turned off the electric field, quickly replaced the solution in the west reservoir with LE, and applied an electric field of 1200 V cm-1. This way, the ITP mode is terminated by injecting LE into the separation channel. Leading ions overtake first trailing ions and then sample ions, thus initiating a separation of sample species by capillary electrophoresis.

Example 7: Selection of the Electrolyte System for Small RNA Isolation and Concentration Using ITP in Microchannels Loaded with Pluronic F-127

Illustrated below is ITP system chemistry for small RNA extraction using ITP in microchannels loaded with Pluronic F-127, which is summarized in Table 1.

TABLE 1

System parameters of the leading and trailing electrolytes

| | pH | Mobility ($m^2V^{-1}s^{-1}$) | Conductivity ($S\ m^{-1}$) | Ionic strength (M) |
|---|---|---|---|---|
| LE[a] | 4.0 | $-68 \times 10^{-9}$ | 0.86 | $1.0 \times 10^{-1}$ |
| TE[b] | 4.0 | $-4 \times 10^{-9}$ | 0.04 | $7.1 \times 10^{-3}$ |

[a]140 mM 6-aminocaproic acid and 100 mM HCl
[b]10 mM 6-aminocaproic acid and 50 mM caproic acid The selection of the electrolyte system is crucial since this allows us to selectively extract and isolate 5 small RNAs from a large variety of other biomolecules present in the cell lysate, including but not limited to pre-miRNAs, mRNAs, rRNAs, DNAs, and proteins. The mobility of small RNAs in our sieving matrix decreases with increasing number of nucleotides. We have searched for and found an effective mobility for our TE which is between the mobility of small RNAs and pre-miRNAs in the sieving matrix, hence separating these species. Again, Table 1 shows the system parameters of the LE and TE; these were determined from simulations using Peakmaster 5.2 for the buffer calculations (including ionic strength dependence). 40 The current density was typically ~2.45×104 A m-2, and this gave sufficient buffering capacity. The minimal ionic strength was ~8 mM during a 5 min ITP experiment and the reservoir size was 5 µL. Therefore, we estimate a change of pH of less than ~0.2 using the Henderson-Hasselbach equation (L. J. Henderson, Am. J. Physiol., 1908, 21, 173-179).

Example 8 Separation of DNA Ladders Using Transient ITP and Sieving Agent

Figure 8A:
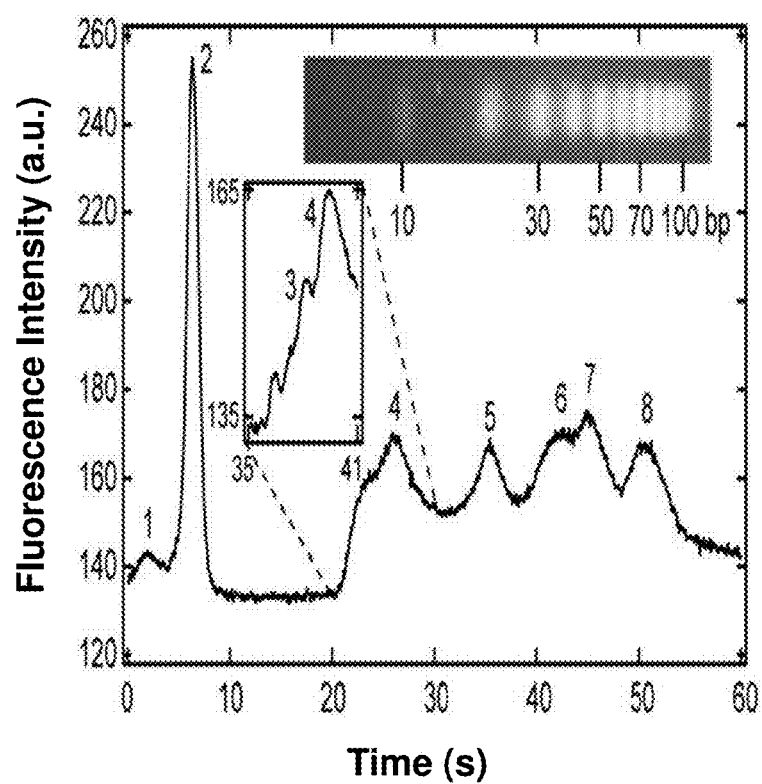
FIGS. 8A and 8B are isotachopherograms of separation in 30% Pluronic F-127 of (A) 10-100 bp DNA ladder, and (B) of 50-800 bp DNA ladder.
Figure 8B:
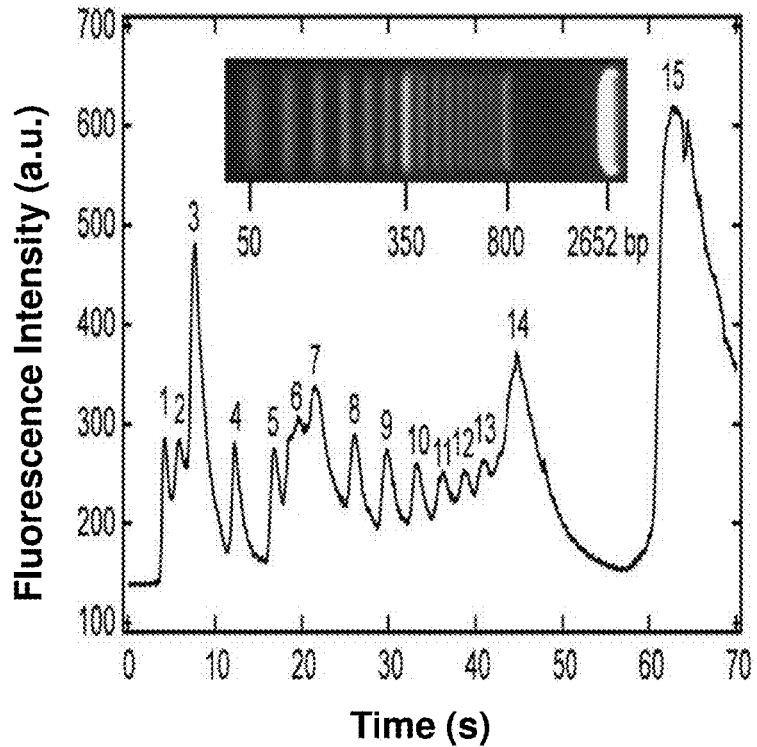

To demonstrate the efficacy of 30% Pluronic F-127, we analyzed the separation of nucleic acids using tITP. FIG. 8A shows the separation of a 10-100 bp DNA ladder (with 10 bp increments). 8 of the 10 fragments were detected without optimization of tITP conditions. According to the supplier, the 10 bp band appears slightly less intense than the other bands (hence the high mobility peak 1 in FIG. 8A). Further, we separated a 50-800 bp DNA ladder (with 50 bp increments, and a vector fragment >2 kbp) as demonstrated in FIG. 8B, and here resolved 15 out of 17 fragments. The 350 bp band is designed by the supplier to be two- to three-times brighter than neighboring bands (hence we identify the intermediate-mobility peak 7 in FIG. 8B). Peak 15 is likely the low-mobility 2652 bp DNA fragment. Although the DNA ladders shown are not perfectly resolved, these experiments confirm that the sieving matrix imparts a significant dependence of electrophoretic mobility on nucleotide length. Below, we demonstrate how we leverage this dependence in selective isolations of small RNAs. In summary, FIG. 8 shows the separation of DNA ladders in 30% Pluronic F-127 using tITP. (a) 8 out of 10 fragments were resolved from a 10-100 bp DNA ladder. The inset shows the magnification of peak 3 and 4, measured further downstream. (b) For the 50-800 bp DNA ladder 15 out of 17 fragments were detected. The LE was 140 mM 6-aminocaproic acid with 100 mM HCl, and the TE was 10 mM Bis-Tris and 50 mM HEPES. The dye was 1×SYBR Green I, and the electric field strength for separation was 1200 V cm-1. The images (from the suppliers) in (a) and (b) show the separation of the DNA ladders in 4% and 2% agarose gels, respectively.

Figure 9:
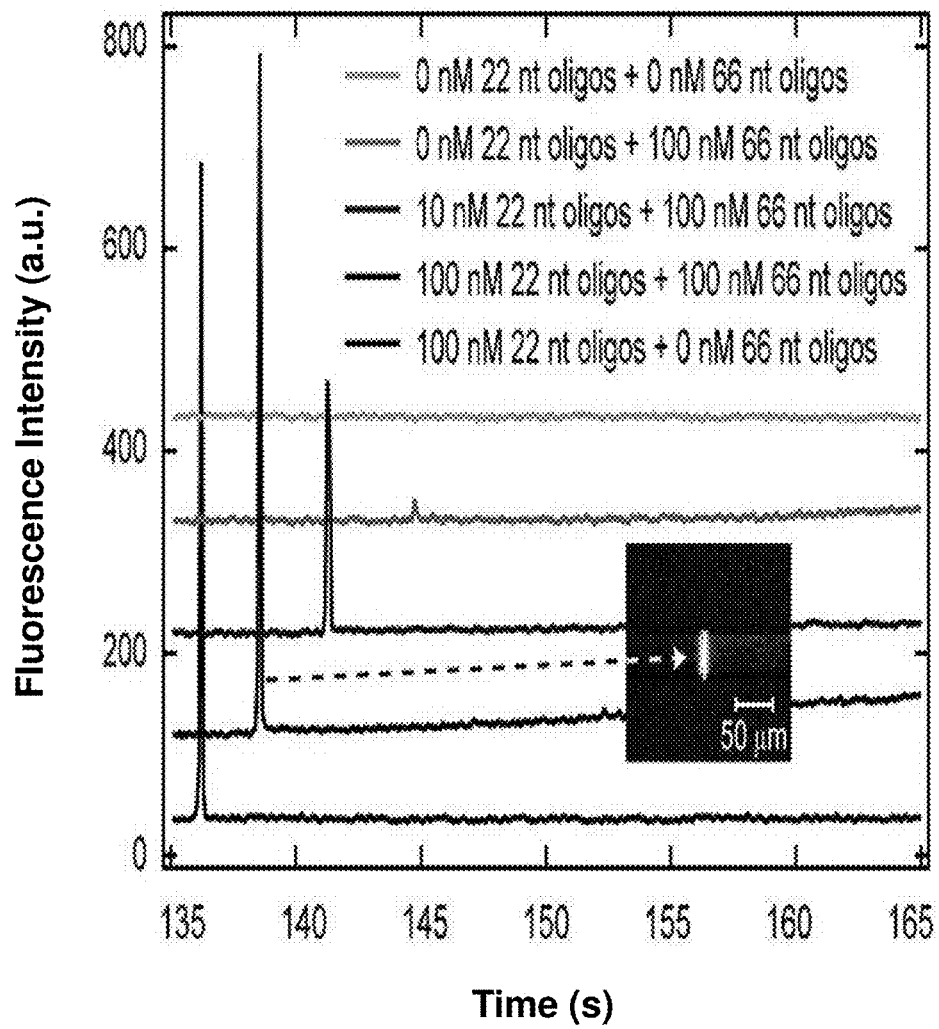
FIG. 9 is a graph showing set of isotachopherograms of extraction and separation of 22 nt from 66 nt oligos in 30% Pluronic F-127. Lines are in order of legend.

Example 9: ITP-Based Extraction and Separation of 22 nt from 66 nt Oligos with Sieving Agent FIG. 9 is a line graph that shows ITP-based extraction and separation of 22 nt from 66 nt oligos in 30% Pluronic F-127. Experimental details are as described in Example 6. The measured signal is dependent only on the 22 nt oligo concentration and independent of the 66 nt oligos. The fluorescence image shows 100 nM 22 nt oligos which are highly focused by ITP in the microchannel. The traces are shifted in time by ~2.5 s (major peaks otherwise approximately line up) and fluorescence intensity to facilitate their comparison. Here, we separated 22 nt from 66 nt oligos, which consisted of only A, C, and G bases. These species have physical properties very similar to small RNAs and pre-miRNAs, respectively. Only 22 nt oligos are focused by ITP as shown by our spiking procedure and control experiments. In all of the experiments shown, the mobility of the TE is higher than our estimates of mobility for oligos of equal or longer length than 66 nt. The top trace shows the baseline control case where no oligos are present. Adding 100 nM of 66 nt oligos results in only a small peak (near 145 s), which we attribute to shorter-oligo impurities from the 66 nt oligo sample (the supplier reports that the sample contains 7% shorter fragments remaining after their purification of the nominal 66 nt oligo sample from polyacrylamide gel electrophoresis). Next, the sample with 10 nM 22 nt oligos and 100 nM 66 nt oligos shows a dramatically increased peak height near 142 s. Spiking the 22 nt oligo sample (100 nM 22 nt oligos and 100 nM 66 nt oligos) clearly results in the increase of the peak (now at 138 s) which we therefore identify as 22 nt oligos. This spiking show that the fluorescence intensity of the peak identified as 22 nt oligos is proportional only to the starting concentration of that species, which is further confirmed in the bottom trace which is spiked with 100 nM 22 nt oligos only.

Example 10: Extraction and Separation of 22 nt Oligos from a 0.1-2 kb RNA Ladder This example demonstrates the separation of 22 nt oligos from a 0.1-2 kb RNA ladder. Data (not shown) showed separations similar to those in Example 6. The fluorescence intensity is proportional to the starting concentration of 22 nt oligos, which focus in the ITP zone between the LE and TE. Note for example the third trace from the top which contained both 22 nt oligos and 0.1-2 kb RNA ladder. Spiking 22 nt oligos at concentrations of 10, 100 and then 1000 nM progressively increases the associated peak intensity (and integrated area) as expected. We attribute the slight peak near 142 s in the top trace to impurities from the RNA ladder.

Figure 10:
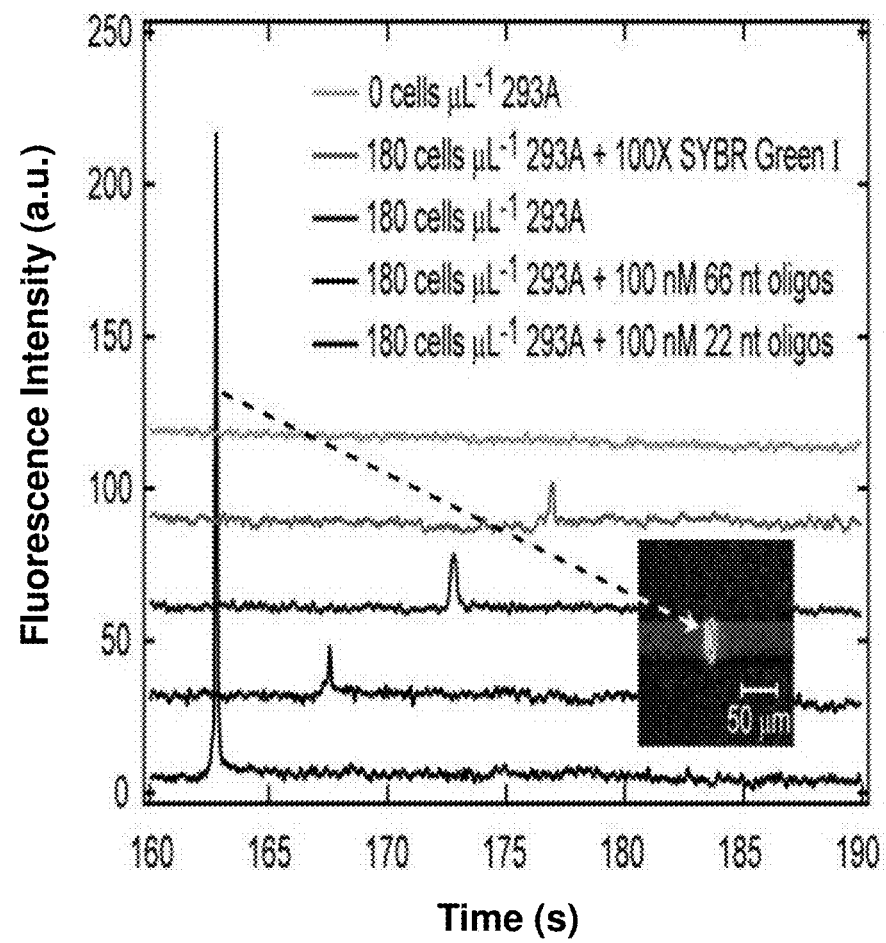
FIG. 10 is a graph showing set of isotachopherograms of extraction and separation of 22 nt oligos from a 0.1-2 kb RNA ladder by isotachophoresis in 30% Pluronic F-127. Lines are in order of legend.

Example 11: Extraction, Isolation and Preconcentration of Small RNAs from 293A Cell Lysate The present ITP-based technique can extract, separate and preconcentrate small RNAs from pre-miRNAs and other biomolecules in lysate of 293A cells. FIG. 10 is again a line graph that summarizes the results of the control, extraction, and spiking experiments. For experimental details, see Example 7. We have shifted the traces in time (here by 5 s) for clarity. The experiments shown in FIG. 10 used 100× SYBR Green II, except for the second trace (from the top) which used 100×SYBR Green I. In the second and third electropherogram, we show that small RNAs from the lysate of 293A cells (at a concentration of 180 cells µL-1) were detected with SYBR Green I and II, respectively. SYBR Green I (designed to bind to dsDNA) intercalates into RNA at a lower quantum yield than SYBR Green 11.28. Consistently, the RNA peak in the third trace has a 15% higher peak height. Spiking the cell lysate with 100 nM 66 nt oligos (fourth trace) results in the same peak shape and intensity for the presumed short (near 22 nt) RNA peak, as expected. Perhaps the strongest evidence is offered by the fifth trace which shows an 11.7 fold signal increase when we spike the lysate with (non-native) 100 nM 22 nt oligos. Clearly, the peak height of the isolated small RNA peak has mobility below 66 nt and nearer to that of 22 nt RNAs. Although not shown here, we have also extracted, isolated and quantitated small RNAs from 10 µg ml$^{-1}$ total RNA samples (processed from embryonic kidney cells (293)), and measured the associated peak heights at ~255 a.u. (data not shown). We have also performed a series of additional calibration experiments with individual 15 oligos and RNA ladders from which we conclude that our ITP extraction process has a cut off near 50 nt as the maximum RNA nucleotide length.

One may approximately quantify the amount of small RNAs in our 293A cell line. The bottommost trace of FIG. 10 was spiked with a known amount of 100 nM 22 nt oligos, and this peak is 11.7 higher intensity than the unspiked sample peak of the third trace, as per the expected, peak mode ITP physics. We can therefore approximate the concentration of small RNAs in the original 25 sample to be 8.6 nM. Considering the concentration of 180 cells µL$^{-1}$, we obtain $2.9 \times 10^7$ small RNAs per cell. Earlier studies have suggested that the total number of piRNAs be on the order of a million fold, and miRNAs are expressed at high levels up to several ten thousands of copies per cell. The total number of types of small RNAs per cell is not known, but we can deduce it by taking the assumption that small RNAs are present at $6 \times 10^4$ copies per cell. This results in an estimate of roughly 500 different types of small RNAs per 293A cell, out of which 122 are known today.

Example 12: Alternative ITP-Based Extraction of DNA and/or RNA from Cell Lysate 22-base oligonucleotides were focused with 280 mM Tris-180 mM Nicotinic Acid (pH 8) as the LE and 17 mM Tris-10 mM 3.5 Dihydroxybenzoic Acid (pH 8) as the TE. TE mM TRIS-10 mM 3.5 DHB were added at the west well (as laid out in FIG. 7A,B,C). RNA was added to the West well. The LE was 280 mM Tris-180 mM nicotinic acid, The LE and TE are designed to focus only short (approximately <200 base) RNA and no other species. The theoretical effective mobility values of the LE and TE are 35×10-9 and 33×10−9 m2 V-1 s-1, respectively. This demonstration experiment was performed by lysing *Pichia pastoris* yeast cells and spiking the lysate with fluorescently labeled 22-base oligonucleotides. We spiked the lysate which had a starting concentration of 60 cells/µL (and a 20 µL sample volume, or approx. 1200 cells) with oligonucleotides, known to have similar physical properties as short RNA. The LE is 280 mM Tris-180 mM Nicotinic Acid (pH 8) and the TE is 17 mM Tris-10 mM 3.5 Dihydroxybenzoic Acid (pH 8). In both LE and TE, 0.25% poly (vinyl-pyrrolidone) is present to dynamically suppress EOF but not act as a sieving matrix.

Example 13: Alternative an-Chip Separation of DNA from a Mixture of 5 Proteins (Using Protein Denaturation)

This experiment shows successful DNA separation from standard proteins, which are major components of genetic samples and major contaminants in sample preparation. In this case, the sample was comprised of 5 proteins (Glucose oxidase, Trypsin inhibitor, Myoglobin, Trypsinogen and Cytochrome C) labeled with Alexa Fluor 488 (Invitrogen), and 1.5 kbp DNA that was amplified by polymerase chain reaction from *Escherichia coli* strain K12. 3 mM salicylic acid and 3 mM valeric acid were added to the sample as spacers in order to separate DNA, proteins, and free/dissociated fluorophore from proteins as demonstrated. DNA was intercalated with SYBR Green I (Invitrogen) for fluorescence detection. Proteins in the sample were denatured with sodium dodecyl sulfate and a heat treatment of 95° C. during 10 minutes in order to achieve uniform mobility of all proteins. 100 mM Tris (tris(hydroxymethyl) amino methane)-50 mM HCl, and 25 mM Tris-192 mM glycine were selected as LE and TE, respectively. The sample was injected between the LE and TE up to a length of 3 mm into the microchannel (70 µm wide and 10 µm deep), and then the electric field of 200 V/cm was applied. The fluorescence was measured at different times, and DNA after a time showed a peak between the proteins (closer to the TE) and the free fluorophore (closer to the LE).

Other protein denaturation agents besides SDS may be used, such as heat, or pH or salts such as urea or guanidine salts or reducing agents which break disulfide bonds. The peptide backbone is left intact.

Example 14: MicroRNA Extraction Using Suppression of Electroosmotic Flow

Figure 11A:
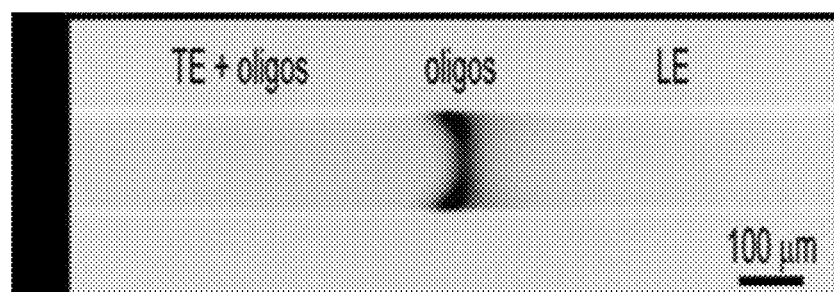
FIGS. 11A and 11B is a reverse-image photograph that shows isotachophoretic purification of 22 nt oligos from oligos (11A) yeast cell lysate (11B).
Figure 11B:
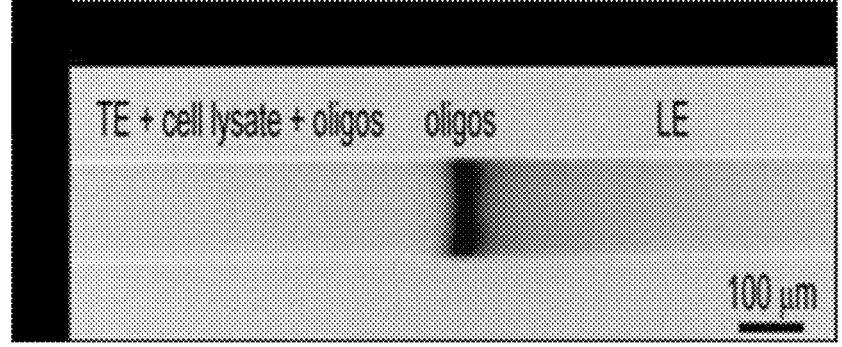

MicroRNAs are small RNA molecules (~18 to 24 nucleotides) that can regulate the expression of genes by binding to messenger RNA. These molecules can be specifically focused by ITP in which the LE and TE have a small mobility difference, and focusing inequalities are met. Using 280 mM Tris-180 mM nicotinic acid at pH 8 as LE, and 17 mM Tris-10 mM 3.5-dihydroxybenzoic acid at pH 8 as TE, their co-ion mobilities are within a few percent of each other. To suppress electro-osmotic flow, 0.25% poly(vinylpyrrolodine) was added to the LE and TE. Oligos with ~18 to 24 nucleotides have similar physical properties as microRNAs and are investigated here. FIG. 11A shows 10 nM 22-base random sequence (A, C, G) oligonucleotides (labeled with Alexa Fluor 488) focused between the LE and TE at an electric field of 190 V/cm. The same molecules at a concentration of 10 nM were spiked in yeast cell lysate (*pichia pastoris*) of 60 cells per µl, and extracted using ITP as demonstrated in FIG. 11B. The microchannel inside the glass chip had a width of 90 µm and a depth of 20 µm. For reproducibility, the images were reversed.

Example 15: $CO_2$ Aided Extraction of 25 bp Ladder from GFP and CAN

Figure 12:
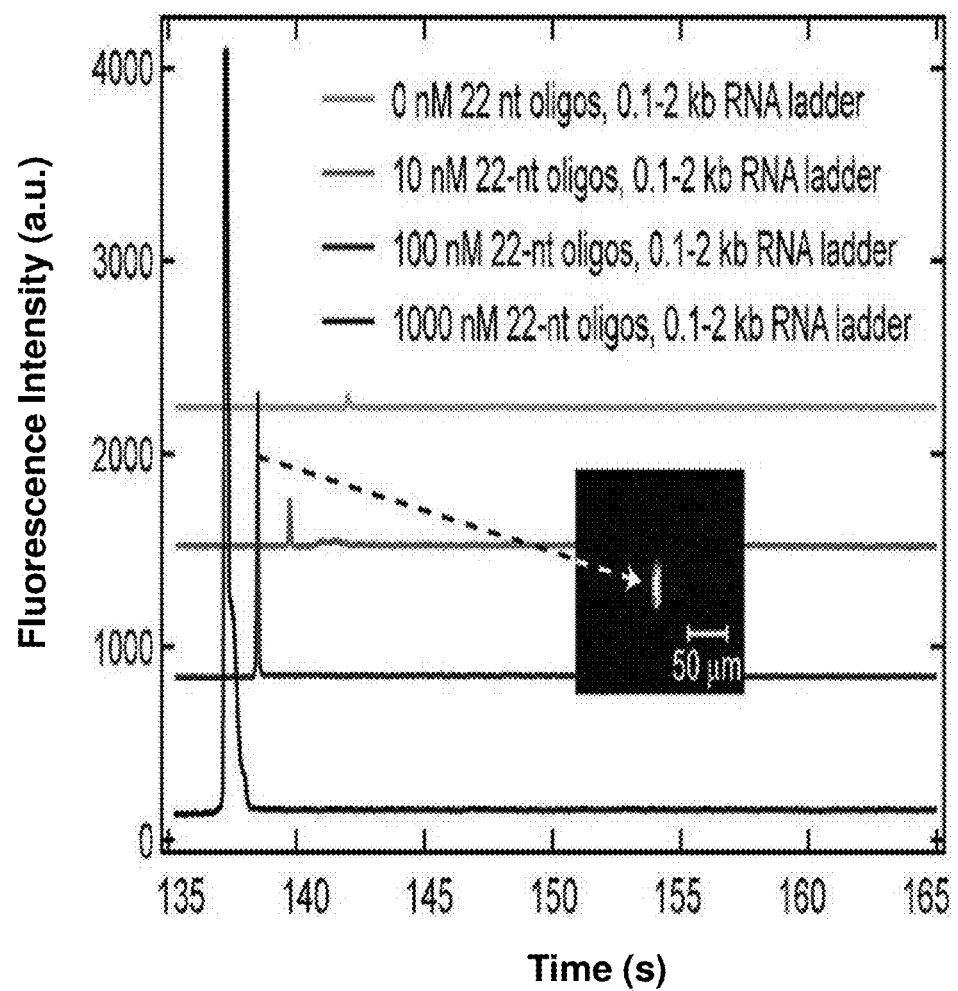
FIG. 12 shows isotachopherograms of atmospheric $CO_2$-aided simultaneous preconcentration and separation of 25 bp DNA ladder from green fluorescent protein (GFP) and allophycocyanin (ACN) in a single interface isotachophoresis experiment. Lines are in order of legend.

FIG. 12 shows a set of isotachopherograms of atmospheric-CO2-aided simultaneous preconcentration and separation of 25 bp DNA ladder from green fluorescent protein (GFP) and allophycocyanin (ACN) in a single interface ITP experiment with 50 mM Tris HCl as the LE and 100 mM Tris glycine as the TE. The electropherograms are obtained 4 s apart and the separated analyte peaks remain focused and dispersion-free as they migrate downstream.

Example 16: Introduction of Counterions in a Multiple Well System

Figure 13:
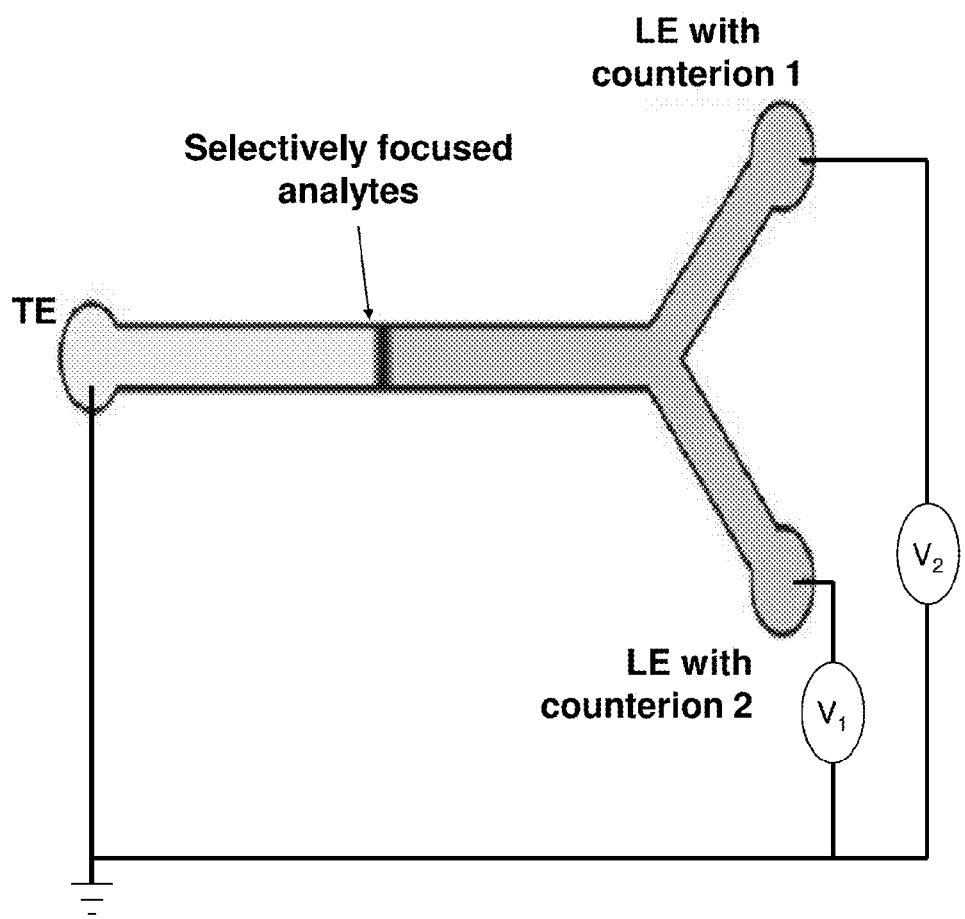
FIG. 13 is a schematic diagram of an exemplary dual-counterion ITP system which can be used to change ITP conditions in real-time. Two different voltages are applied to two branches.

FIG. 13 shows a dual-counterion ITP system where both LE wells contain the same leading ion, but different counterions. The applied voltages $V_1$ and $V_2$ control the ratios of the two counterions in the separation channel. More wells allow additional degrees of freedom.

For example, the two LE wells shown in the figure control the pH of the TE. Alternatively, the two wells can be configured to control the pH of the LE. A third LE well allows control of both simultaneously. Additional wells allow control of, for example, the concentration of a sieving matrix or complex-forming counterion. FIG. 13 illustrates channel bifurcation in which analytes can be distributed to various channels. It can be envisioned that a number of bifurcations or junctions can be designed to distribute different fractions into different channels, using the basic design of FIG. 13. For example, the target nucleic acid can be separated from protein, which goes into one channel and small molecules, which go in to another channel.

CONCLUSION

The above specific description is meant to exemplify and illustrate the invention and should not be seen as limiting the scope of the invention, which is defined by the literal and equivalent scope of the appended claims. Any patents or publications mentioned in this specification are intended to convey details of methods and materials useful in carrying out certain aspects of the invention which may not be explicitly set out but which would be understood by workers in the field. Such patents or publications are hereby incorporated by reference to the same extent as if each was specifically and individually incorporated by reference and contained herein, as needed for the purpose of describing and enabling the method or material referred to.

---

---

What is claimed is:

1. An isotachophoretic method for concentrating a target nucleic acid and for separating said target nucleic acid from at least one other macromolecule in a sample, said method comprising the steps of:

(a) applying a sample comprising a mixture of a target nucleic acid and ionic macromolecules that are not target nucleic acids to a sample well connected to at least one liquid channel;

(b) causing said sample comprising said mixture of a target nucleic acid and ionic macromolecules that are not target nucleic acids to be in contact with a trailing electrolyte (TE) and a leading electrolyte (LE) in said at least one liquid channel, said TE having an effective-mobility magnitude greater than at least one of said ionic macromolecules that are not target nucleic acids and less than said target nucleic acid, said LE having an effective-mobility magnitude greater than said target nucleic acid, and wherein said LE and TE contacting said sample are in free solution, and are at a pH of from 4 to 10; and (c) applying a voltage difference along said at least one liquid channel, said at least one liquid channel containing said sample, said LE, and said TE, to cause concentration of said target nucleic acid in an isotachophoresis interface between LE and TE and separation of said at least one of said ionic macromolecules that are not target nucleic acids from said isotachophoresis interface between LE and TE.

2. The method of claim 1 wherein said sample well and said at least one liquid channel are located within a microfluidic device.

3. The method of claim 1 further comprising adding a polymer sieving agent to said at least one liquid channel to change an effective-mobility magnitude of one or both of said target nucleic acid and said at least one of said ionic macromolecules that are not target nucleic acids.

4. The method of claim 3 wherein said sieving agent is selected from the group consisting of block copolymer, linear polymers, and cross-linked polymers.

5. The method of claim 1 further comprising adding an agent for suppressing electroosmotic flow to said at least one liquid channel.

6. The method of claim 5 wherein said agent for suppressing electroosmotic flow is selected from the group consisting of polylactams, substituted polyacrylamide derivatives, water soluble methylhydroxyethyl derivatives of cellulose, polyvinylalcohol, polyvinylpyrrolidones and polyethyleneglycols.

7. The method of claim 6 wherein said polylactam is polyvinylpyrrolidone.

8. The method of claim 1 wherein said at least one liquid channel divides at channel bifurcations to distribute various contents of said sample to various channels.

9. The method of claim 1, wherein said sample is treated with a cell lysis agent prior to applying said sample to said sample well.

10. The method of claim 1, wherein said sample is treated with a cell release agent to release said target nucleic acid from bound protein, if present, prior to applying said sample to said sample well.

11. The method of claim 10 wherein said release agent is a protease.

12. The method of claim 1 wherein said sample is mixed with said TE prior to entering said at least one liquid channel.

13. The method of claim 1 further comprising removing concentrated target nucleic acid from an interface between said LE and said TE.

14. The method of claim 1 wherein said target nucleic acid is genomic DNA.

15. The method of claim 1, wherein said at least one liquid channel is a liquid microchannel.

16. The method of claim 1, wherein said sample is mixed with said LE prior to entering said at least one liquid channel.

17. The method of claim 1, wherein said at least one liquid channel is connected to a channel comprising said LE and a channel comprising said TE.

18. The method of claim 1, wherein said sample contacts said LE and TE in said at least one liquid channel at the same time.

19. The method of claim 1, wherein said sample contacts said TE prior to contacting said LE in said at least one liquid channel.

20. The method of claim 1, wherein said sample contacts said LE prior to contacting said TE in said at least one liquid channel.

21. The method of claim 1, wherein said sample is mixed with a spacer prior to entering said at least one liquid channel.

22. The method of claim 1, wherein said target nucleic acid is RNA.

23. The method of claim 1, wherein said target nucleic acid comprises DNA and RNA.

24. The method of claim 1, wherein said at least one of said ionic macromolecules that are not target nucleic acids comprise protein.

25. The method of claim 1, wherein said target nucleic acid comprises DNA and said ionic macromolecules that are not target nucleic acids comprise protein.

26. The method of claim 1, wherein said method does not cause focusing of said at least one of said non-target ionic macromolecules in an isotachophoresis interface.

27. The method of claim 1, wherein mobility of said LE and said TE is parallel to an electric field produced by said voltage difference.

28. The method of claim 1, wherein said sample is selected from the group consisting of: whole blood, serum, and plasma.

29. The method of claim 28, wherein said sample is a whole blood sample.

30. The method of claim 28, wherein said sample is a plasma sample.

31. The method of claim 1, wherein said sample comprises lysed cell membranes.

32. The method of claim 1, wherein said sample comprises whole cells.

33. The method of claim 1, wherein said sample further comprises buffer or water.

34. An isotachophoretic method for concentrating small RNA from a sample comprising a mixture of macromolecules comprising small RNA, proteins, and longer RNA, comprising:

(a) applying a sample comprising a mixture of macromolecules comprising small RNA, proteins, and longer RNA to a sample well connected to at least one liquid channel;

(b) causing said sample comprising a mixture of macromolecules comprising small RNA, proteins, and longer RNA to be in contact with a trailing electrolyte (TE) and a leading electrolyte (LE) in said at least one liquid channel, said TE having an effective-mobility magnitude less than said small RNA and greater than said proteins in the sample, and said LE having an effective-mobility magnitude greater than said small RNA, wherein said LE and said TE are in free solution, and are at a pH which causes effective mobility of proteins to be different from that of the small RNA; and (c) applying a voltage along said at least one liquid channel containing said sample, said LE, and said TE to cause concentration of said small RNA in an isotachophoresis interface between said LE and said TE, and to cause separation of said proteins and longer RNA from said isotachophoresis interface between said LE and said TE, wherein said LE and said TE are at a pH which causes effective mobility of proteins to be lower than that of said small RNA.

35. The method of claim 34 further comprising the step of treating said sample with an RNAse inhibitor.

36. The method of claim 34 further comprising adding a sieving agent to said LE.

37. The method of claim 36 wherein said sieving agent is a block copolymer of ethylene oxide and propylene oxide.

38. The method of claim 34 further comprising treating said sample with one or more of DNAse and protease.

39. The method of claim 38 wherein said protease is Proteinase K.

40. The method of claim 34 further comprising adding a protein denaturing agent to said at least one liquid channel.

41. The method of claim 34 wherein said sample is mixed with said TE prior to entering said at least one liquid channel.

* * * * *

SEQUENCE LISTING

```
<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic

<400> SEQUENCE: 1
caccttgtga tgttagtttg ga                                              22

<210> SEQ ID NO 2
<211> LENGTH: 22
<212> TYPE: DNA
<213> ORGANISM: Artificial Sequence
<220> FEATURE:
<223> OTHER INFORMATION: Synthetic

<400> SEQUENCE: 2
tggaaaagac ttgcttggta ct                                              22
```